(12) United States Patent
Leproust et al.

(10) Patent No.: US 7,070,932 B2
(45) Date of Patent: Jul. 4, 2006

(54) METHODS AND DEVICES FOR DETECTING PRINTHEAD MISALIGNMENT OF AN IN SITU POLYMERIC ARRAY SYNTHESIS DEVICE

(75) Inventors: Eric M. Leproust, Campbell, CA (US); Douglas A. Amorese, Los Altos, CA (US); Mel N. Kronick, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 421 days.

(21) Appl. No.: 10/374,307

(22) Filed: Feb. 25, 2003

(65) Prior Publication Data

US 2004/0170984 A1  Sep. 2, 2004

(51) Int. Cl.
*C07H 21/04* (2006.01)
*C12Q 1/68* (2006.01)

(52) U.S. Cl. .................... 435/6; 435/91.1; 435/91.2; 536/23.1; 536/24.3

(58) Field of Classification Search ............... None
See application file for complete search history.

(56) References Cited

U.S. PATENT DOCUMENTS

| | | | |
|---|---|---|---|
| 6,232,072 B1 | 5/2001 | Fisher | |
| 6,284,465 B1 | 9/2001 | Wolber | |
| 6,300,137 B1 | 10/2001 | Earhart et al. | |
| 2003/0148539 A1* | 8/2003 | van Dam et al. | ........... 436/180 |

OTHER PUBLICATIONS

Khan et al. (Genomics, vol. 81, pp. 157-165, Feb. 20, 2003).*

* cited by examiner

*Primary Examiner*—Jeanine A. Goldberg

(57) ABSTRACT

Methods and devices for detecting deposition unit misalignment, e.g., printhead misalignment, of an in situ polymeric, e.g., a nucleic acid, array synthesis device are provided. In accordance with the subject methods, at least one test probe feature is synthesized on a substrate using an in situ polymeric array, e.g., nucleic acid array or protein array, synthesis device. The at least one test probe feature is then contacted with at least two different distinguishably labeled targets, e.g., target nucleic acids. The binding of the targets to the at least one test probe feature is then evaluated to detect any misalignment, e.g., deposition unit or pulse jet misalignments, of the synthesis device. Also provided are substrates having at least one test probe feature and at least one polymeric array, as well as methods of using the substrates in array assays. Also included are kits for use in practicing the subject methods.

27 Claims, 14 Drawing Sheets

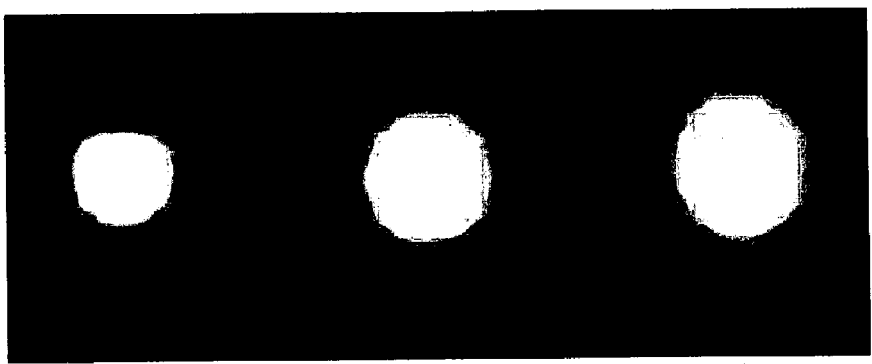
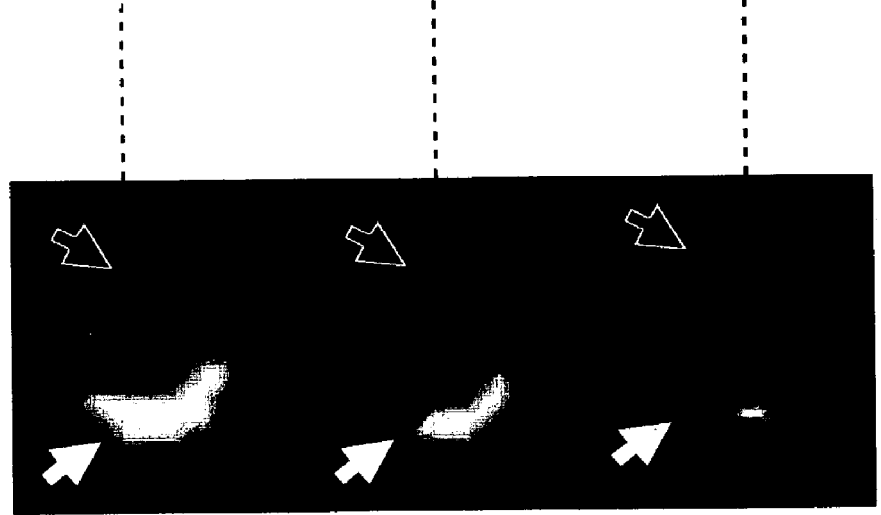
FIG. 12B
FIG. 12A
Alignment #1
Alignment #2
Alignment #3
White arrows show Cy3 signal
Grey arrows show Cy5 signal

METHODS AND DEVICES FOR DETECTING PRINTHEAD MISALIGNMENT OF AN IN SITU POLYMERIC ARRAY SYNTHESIS DEVICE

FIELD OF THE INVENTION

The field of this invention is biopolymeric arrays.

BACKGROUND OF THE INVENTION

Array assays between surface bound binding agents or probes and target molecules in solution may be used to detect the presence of particular analytes or biopolymers in a solution. The surface-bound probes may be oligonucleotides, peptides, polypeptides, proteins, antibodies or other molecules capable of binding with target biomolecules in the solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution suspected of containing an analyte or target molecule(s) ("target(s)") that binds with the attached probes is placed in contact with the bound probes under conditions sufficient to promote binding of targets in the solution to the complementary probes on the substrate to form a binding complex that is bound to the surface of the substrate. The pattern of binding by target molecules to probe features or spots on the substrate produces a pattern, i.e., a binding complex pattern, on the surface of the substrate which is detected. This detection of binding complexes provides desired information about the target biomolecules in the solution.

The binding complexes may be detected by reading or scanning the array with, for example, optical means, although other methods may also be used, as appropriate for the particular assay. For example, laser light may be used to excite fluorescent labels attached to the targets, generating a signal only in those spots on the array that have a labeled target molecule bound to a probe molecule. This pattern may then be digitally scanned for computer analysis. Such patterns can be used to generate data for biological assays such as the identification of drug targets, single-nucleotide polymorphism mapping, monitoring samples from patients to track their response to treatment, assessing the efficacy of new treatments, etc.

There are two main ways of producing polymeric arrays in which the immobilized polymers are covalently attached to the substrate surface: via in situ synthesis in which the polymers are grown on the surface of the substrate in a step-wise fashion and via deposition of the full polymer, e.g., a pre-synthesized nucleic acid/polypeptide, cDNA fragment, etc., onto the surface of the array.

Where the in situ synthesis approach is employed, conventional phosphoramidite synthesis protocols are typically used. In phosphoramidite synthesis protocols, the 3'-hydroxyl group of an initial 5'-protected nucleoside is first covalently attached to the polymer support, e.g., a planar substrate surface.

Synthesis of the nucleic acid then proceeds by deprotection of the 5'-hydroxyl group of the attached nucleoside, followed by coupling of an incoming nucleoside-3'-phosphoramidite to the deprotected 5' hydroxyl group (5'-OH). The resulting phosphite triester is finally oxidized to a phosphotriester to complete the internucleotide bond. The steps of deprotection, coupling and oxidation are repeated until a nucleic acid of the desired length and sequence is obtained.

It will be apparent that the effectiveness of employing these arrays depends on the precision with which these oligonucleotides can be synthesized on the substrate surface. As with any chemical process, certain factors may cause the yields of specific steps in the synthesis of oligonucleotides to be less than 100%, resulting in unintended or unwanted intermediate species.

Oftentimes in situ synthesis is carried-out by way of highly automated methods that employ in situ fluid deposition synthesis devices such as pulse-jet fluid deposition devices in which thermal or piezo pulse jet devices analogous to inkjet printing devices are employed to deposit fluids of biopolymeric precursor molecules, i.e., monomers, onto a substrate surface. For example, Roda et al., Biotechniques (2000) 28:492–496, describe a method in which a conventional inkjet printer is used for the microdeposition of proteins. In this report, the black ink was removed from a Hewlett Packard ink cartridge and the cartridge was extensively washed with water. The cartridge was filled with the protein deposition solution using a microsyringe and sealed. U.S. patents disclosing thermal and/or piezo pulse jet deposition of biopolymer containing fluids onto a substrate include: U.S. Pat. Nos. 4,877,745; 5,449,754; 5,474,796; 5,658,802; 5,700,637; 5,958,342; 6,015,880 and 6,419,883. Other in situ fluid deposition synthesis methods and devices such as those that employ other technology such as spotting a fluid with a pin or acoustical focusing may also be employed for in situ synthesis.

In this manner, a series of droplets, each containing one particular type of reactive deoxynucleoside phosphoramidite is sequentially applied to each discrete area or "feature", sometimes referred to as a "spot", of the array by a pulse-jet printhead or other analogous technology. The inventors have realized that, unfortunately, the precision at which successive droplets can be applied to a feature is insufficient to guarantee that each successive droplet is deposited at the precise location to which it is intended, i.e., to ensure that each successive droplet is confined to the intended feature area or that the entire feature will be covered by any particular droplet. Misalignment of successively applied droplets may lead to significant amounts of undesirable polymers that are unintentionally synthesized along with a desired polymer within each feature, and may, in addition, lead to synthesis of unwanted polymers in regions of the surface of the array substrate adjacent to each feature.

More specifically, during fabrication of in situ oligonucleotide arrays, the oligonucleotide synthesis cycle is spatially controlled to initiate synthesis and perform successive couplings at specific locations on the substrate surface. Accordingly, coupling of the phosphoramidites is spatially controlled using pulse-jet fluid deposition technology (or other suitable technology) and the remainder of the steps, e.g., capping, oxidation, etc., is performed in a flow cell. Consequently, during the synthesis of each successive oligonucleotide layer, the solid support is transferred between a stage such as an XYZ stage of a spatially controlled reaction module for coupling and a non-spatially controlled reaction module for optionally capping, oxidation, etc. Therefore, spatial registration and alignment is necessary prior to coupling in the spatially controlled reaction module to ensure that the phosphoramidite reagents are delivered at the same locations as the previous reagents. The inventors have realized that a shift or misalignment in the stage position and/or in the alignment of one or more of the deposition heads of the spatially controlled reaction module results in a misalignment in the location of the delivered droplets of phosphoramidites reagents at different layers of the synthesis. Consequently, the inventors have realized that a mixture of full length or intended sequences and unintended sequences may be produced if misalignment occurs.

FIG. 1 shows the result of such a misalignment as realized by the inventors where a two step synthesis process, i.e., a two-layer synthesis made of two nucleotides, i.e., a dinucleotide, is illustrated. The misalignment during synthesis may be due the misalignment of the printheads and results in a first layer or first droplet 112 that includes a first deposited nucleoside and a second layer or second droplet 114 that includes a second deposited nucleoside, where the two layers are not correctly positioned with respect to each other. As shown, the inventors have realized that due to the misalignment, three discrete regions are produced instead of a desired single region having the full length intended nucleic acid that would have been the result if no misalignment occurred. Accordingly, region 113 is made-up of only the first nucleotide. A misalignment causes the second layer to be shifted with respect to the first layer resulting in a region 115 that is made-up of only the second nucleotide. Due to a portion of the second droplet overlaying a portion of the first droplet, third region 116 is also produced and includes the intended full length sequence made-up of both first and second nucleotides coupled together, i.e., a dinucleotide. This misalignment can be repeated for each sequential nucleotide addition and between cycles of an in situ synthesis process.

Furthermore, the synthesized oligonucleotides may be composed of one or more of, oftentimes all of, four different nucleotides in a particular sequence, where the nucleotides may be delivered by pulse-jet fluid deposition printheads during coupling in the spatially controlled reaction module. Typically, these printheads include one or more nozzles or apertures thereon, through which a precursor reagent, e.g., a particular nucleotide, is dispensed. The precursor reagents are typically contained within one or more reagent reservoirs that are associated with the printheads, and more specifically one or more nozzles of a printhead. The number of nozzles per reservoir or per printhead may vary and may range from about 2 about 1024, e.g., from about 20 to about 256. Accordingly, the number of printheads employed may vary and may range from four printheads such that each type of nucleotide may be deposited by an individual, independent printhead to two printheads such that two types of nucleotides may be delivered by a single printhead having two reagent reservoirs associated therewith.

Thus, the inventors have realized that the relative misalignment between two printheads may therefore be determined by the relative alignment of the printhead nozzles with respect to each other, e.g., a nozzle of one printhead relative to a nozzle of another printhead. Accordingly, the inventors have realized that a misalignment of any of these printheads, or rather the nozzles of the printheads, relative to each other will produce a mixture of full length sequences, i.e., intended sequences, and unintended sequences.

Regardless of how the unintended sequences are produced, when contacted with a sample containing labeled target molecules during an array assay, not only can the full length intended sequence bind labeled target molecules in the sample, but also one or more unintended sequences can bind labeled target molecules in the sample. The inventors have realized that the presence of these undesirable polymers produced on the substrate surface may lead to less specific binding of radioactively, fluorescently or chemiluminescently labeled target to the array, which may in turn lead to a significant decrease in the signal-to-noise ratio in the analysis of the array which may compromise array assay results, e.g., if all of the pixels from the features are used in the data analysis.

Accordingly, there continues to be an interest in the development of new methods and devices to detect any printhead misalignments of an in situ nucleic acid array synthesis fluid deposition device. Of particular interest is the development of such methods and devices that are easy to use, cost effective, effective at detecting printhead misalignments and which may enable immediate detection and/or adjustments of one or more printheads of an in situ nucleic acid array synthesis fluid deposition device if misalignment is detected.

SUMMARY OF THE INVENTION

Methods and devices for detecting deposition unit misalignment, e.g., printhead misalignment, of an in situ polymeric, e.g., a nucleic acid, array synthesis device are provided. In accordance with the subject methods, at least one test probe feature is synthesized on a substrate using an in situ polymeric array, e.g., nucleic acid array, synthesis device. The at least one test probe feature is then contacted with at least two different distinguishably labeled targets, e.g., target nucleic acids. The binding of the targets to the at least one test probe feature is then evaluated to detect any misalignment of the in situ polymeric array synthesis device. In certain embodiments, one or more deposition units (which may be pulse jets) are adjusted based on any detected misalignment, for example prior to synthesizing a nucleic acid or protein array using the in situ polymeric synthesis device, where the polymeric array may be synthesized on the same substrate that carries the at least one test probe feature or another substrate. The subject invention also includes substrates having at least one test probe feature and at least one polymeric array, e.g., a nucleic acid or protein array, thereon, as well as methods of using the substrates in array assays. Also included are kits for use in practicing the subject methods.

BRIEF DESCRIPTIONS OF THE DRAWINGS

Figure 8A:
Figure 8B:
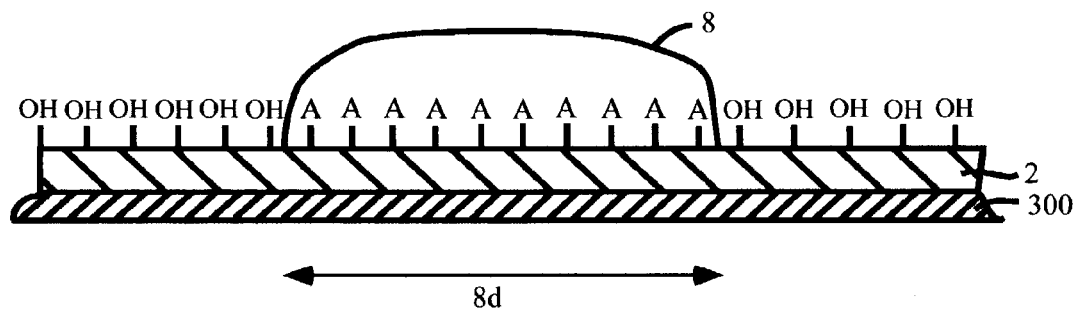
Figure 8C:
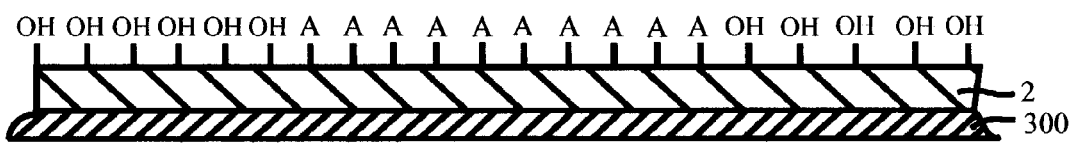
Figure 8D:
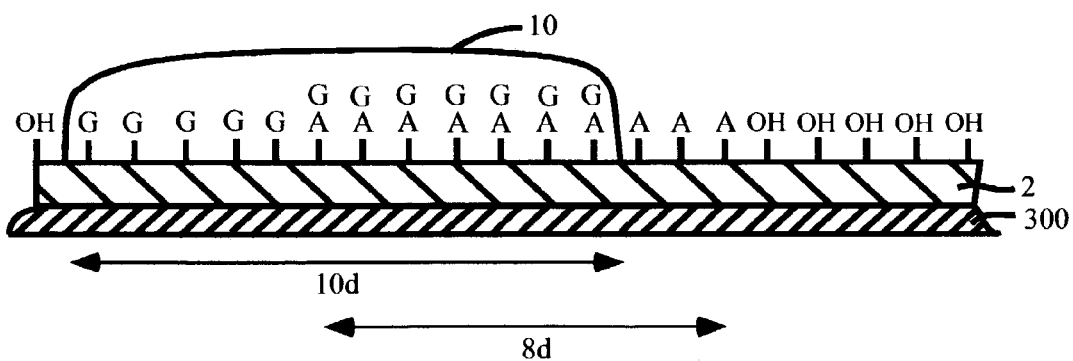
Figure 8E:
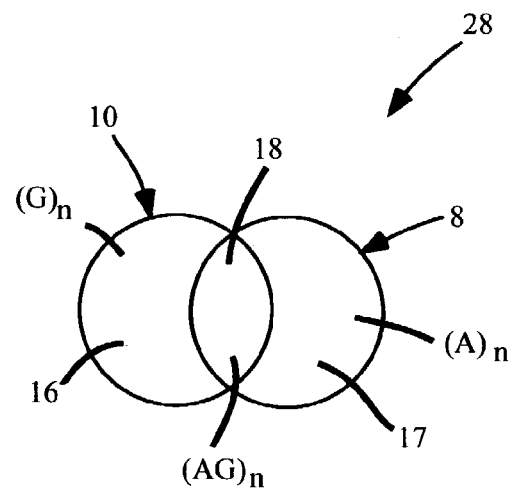
Figure 8F:
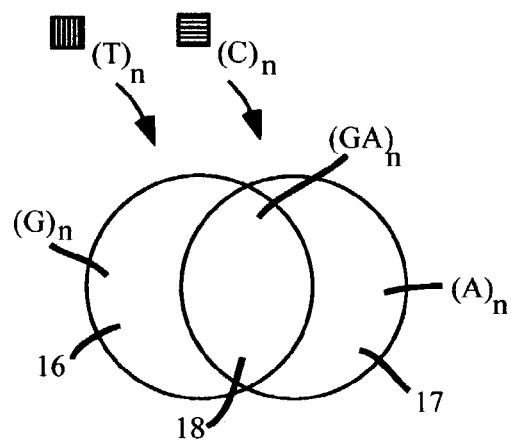
Figure 8G:
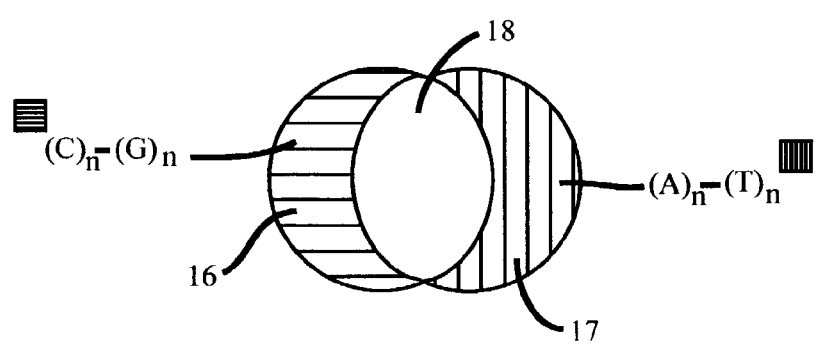
Figure 8H:
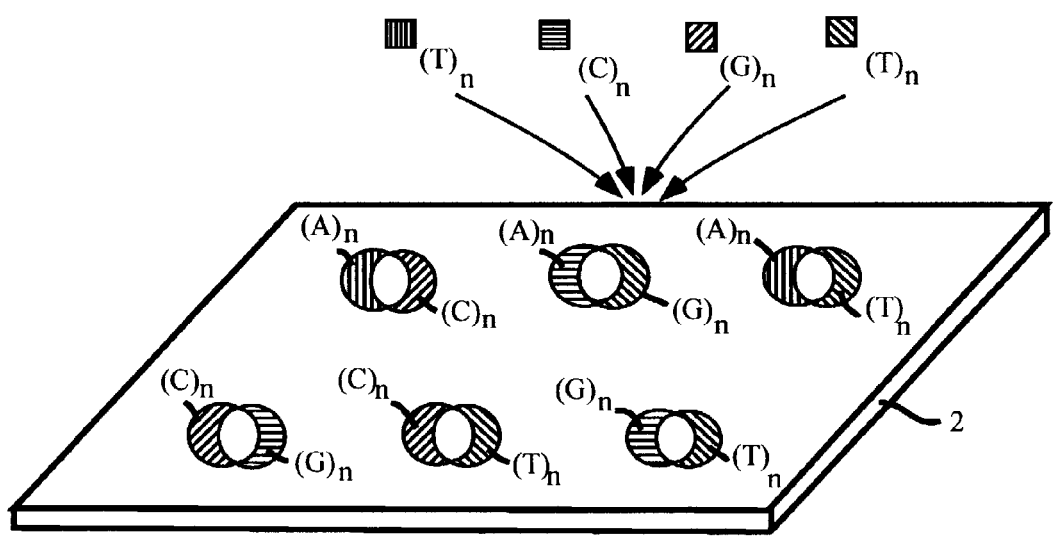

FIGS. 8A–8G illustrate the steps of an exemplary embodiment of the subject methods wherein FIGS. 8A–8E illustrate the steps of synthesizing a test probe feature on a substrate according to the subject invention and FIGS. 8F–8H illustrate the steps of using the synthesized test probe feature to detect printhead misalignment and FIG. 8G illustrates a plurality of test probe features employed to detect printhead misalignment.

Figure 9A:
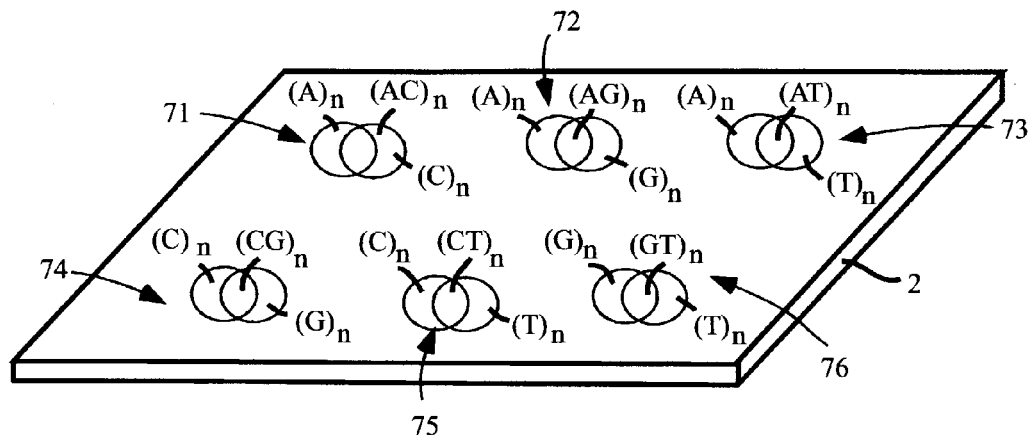
Figure 9B:
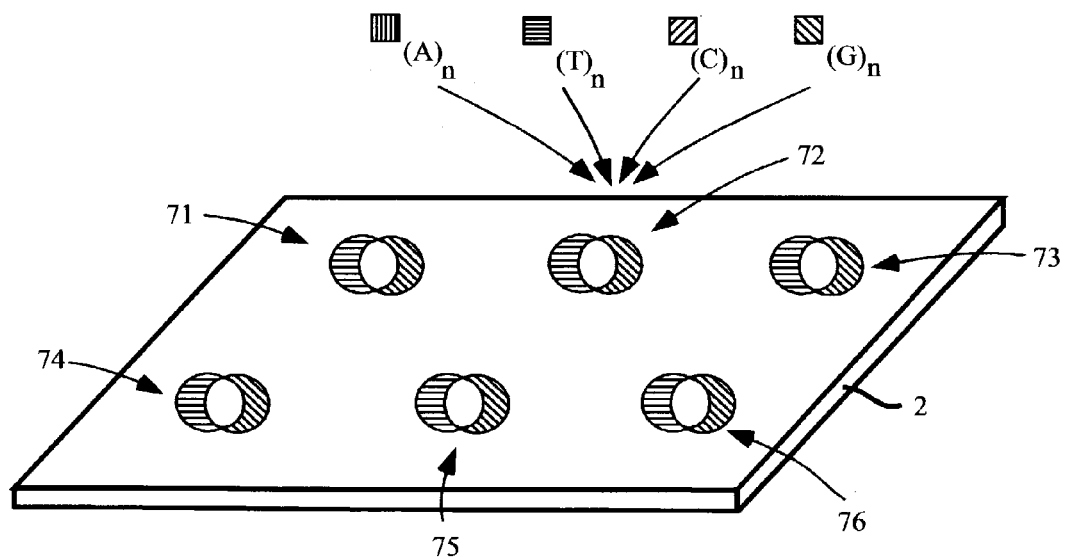

FIGS. 9A–9B illustrate the steps of another exemplary embodiment of the subject methods wherein FIG. 9A illustrates the synthesis of test probe features on a substrate surface and FIG. 9B illustrates the steps of using the synthesized test probe features to detect printhead misalignment.

Figure 10A:
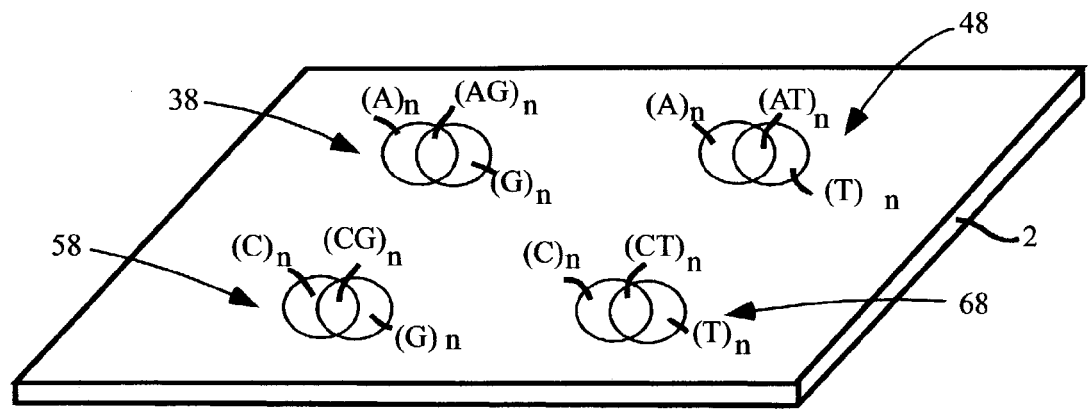
Figure 10B:
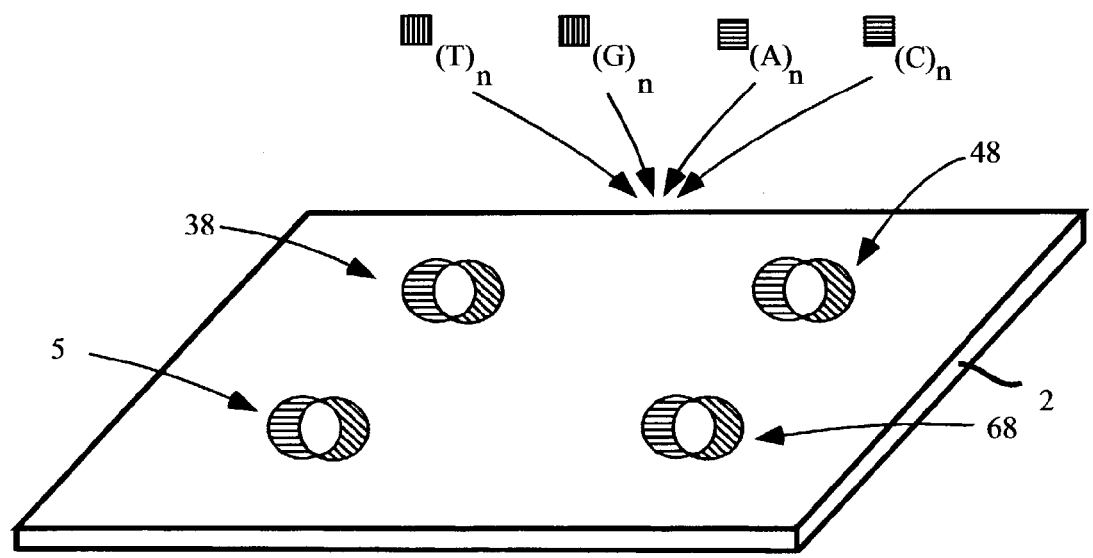

FIGS. 10A–10B illustrate the steps of another exemplary embodiment of the subject methods wherein FIG. 10A illustrates the synthesis of test probe features on a substrate surface and FIG. 10B illustrates the steps of using the synthesized test probe features to detect printhead misalignment.

Figure 11A:
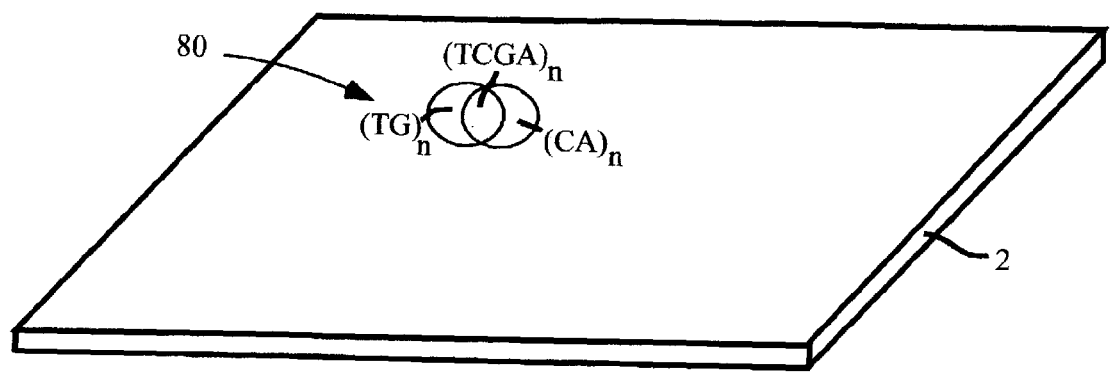
Figure 11B:
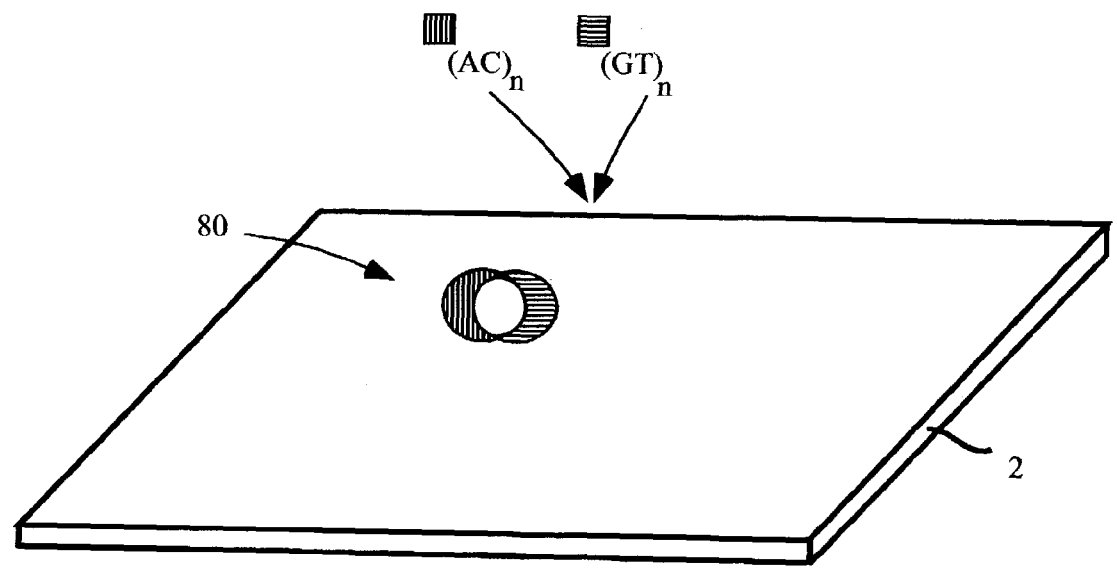

FIGS. 11A–11B illustrate the steps of another exemplary embodiment of the subject methods wherein FIG. 11A illustrates the synthesis of a test probe feature on a substrate surface and FIG. 11B illustrates the steps of using the synthesized test probe feature to detect printhead misalignment.

FIGS. 12A and 12B show the fluorescent signals that resulted from employing the subject methods to detect relative alignment between printheads.

DEFINITIONS

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in hybridization reactions, i.e., cooperative interactions through Pi electrons stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The term "monomer" as used herein refers to a chemical entity that can be covalently linked to one or more other such entities to form an oligomer. Examples of "monomer" include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). The initial substrate-bound monomer is generally used as a building-block in a multi-step synthesis procedure to form a complete polymer or ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

"Optional" or "optionally" means that the subsequently described circumstance may or may not occur, so that the description includes instances where the circumstance occurs and instances where it does not. For example, the phrase "optionally capping" means that a capping step may or may not be performed, and, thus, the description includes embodiments wherein a capping step is performed and embodiments wherein a capping step is not performed.

An "array," includes any two-dimensional or substantially two-dimensional (as well as a three-dimensional) arrangement of addressable regions bearing a particular chemical moiety or moieties (e.g., biopolymers such as polynucleotide or oligonucleotide sequences (nucleic acids), polypeptides (e.g., proteins), carbohydrates, lipids, etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of a substrate. Depending upon the use, any or all of the arrays may be the same or different from one another and each may contain multiple spots or features. A typical array may contain more than ten, more than one hundred, more than one thousand, more than ten thousand features, or even more than one hundred thousand features, in an area of less than 20 cm$^2$ or even less than 10 cm$^2$. For example, features may have widths (that is, diameter, for a round spot) in the range from a 10 µm to 1.0 cm. In other embodiments each feature may have a width in the range of 1.0 µm to 1.0 mm, usually 5.0

μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, a substrate may transmit at least 20%, or 50% (or even at least 70%, 90%, or 95%), of the illuminating light incident on the front as may be measured across the entire integrated spectrum of such illuminating light or alternatively at 532 nm or 633 nm.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features may be, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

"Remote location," means a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

"Communicating" information references transmitting the data representing that information as electrical signals over a suitable communication channel (e.g., a private or public network).

"Forwarding" an item refers to any means of getting that item from one location to the next, whether by physically transporting that item or otherwise (where that is possible) and includes, at least in the case of data, physically transporting a medium carrying the data or communicating the data.

The terms "reporter," "label" "detectable reporter" and "detectable label" refer to a molecule capable of generating a measurable signal, including, but not limited to, fluorescers, and the like. The term "fluorescer" refers to a substance or a portion thereof which is capable of exhibiting fluorescence in the detectable range when excited at the appropriate wavelength. Particular examples of labels which may be used under the invention include, but are not limited to: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G), 1,1,3,3,3',3'-Hexamethylindodicarbocyanine iodide (HIDC), 6-carboxyfluorescein (commonly known by the abbreviations FAM and F),6-carboxy-2-,4-,7-,4,7-hexachlorofluorescein (HEX), 6-carboxy-4', 5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, and the like.

DETAILED DESCRIPTION OF THE INVENTION

Methods and devices for detecting deposition unit misalignment, e.g., printhead misalignment, of an in situ polymeric, e.g., a nucleic acid, array synthesis device are provided. In accordance with the subject methods, at least one test probe feature is synthesized on a substrate using an in situ polymeric array, e.g., nucleic acid array or protein array, synthesis device. The at least one test probe feature is then contacted with at least two different distinguishably labeled targets, e.g., target nucleic acids. The binding of the targets to the at least one test probe feature is then evaluated to detect any misalignment of the in situ polymeric array synthesis device. In certain embodiments, one or more deposition units are adjusted based on any detected misalignment, for example prior to synthesizing a nucleic acid or protein array using the in situ polymeric synthesis device, where the polymeric array may be synthesized on the same substrate that carries the at least one test probe feature or another substrate. The subject invention also includes substrates having at least one test probe feature and at least one polymeric array, e.g., a nucleic acid or protein array, thereon, as well as methods of using the substrates in array assays. Also included are kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, the subject invention includes methods of detecting any misalignment of printheads relative to each other of an in situ polymeric array synthesis device. As mentioned above, such an in situ polymeric array synthesis device may be employed in the in situ fabrication of a polymer such as a nucleic acid or protein or other polymeric entities on a substrate surface using drop deposition from a deposition unit such as a pulse jet deposition unit of reagents of precursor units or residues (i.e., monomers) such that the precursor units are deposited or "layered" in a sequential fashion and bonded together to form the desired polymer, e.g., a nucleic acid or polypeptide, on the surface of the substrate. As such, these deposition devices may be referred to as polymeric array synthesis devices, nucleic acid synthesis devices, protein or polypeptide synthesis devices, etc., where the use herein of any of such references is in no way intended to be limiting. In further describing the subject invention, reference is made primarily to an in situ nucleic acid synthesis device as well as nucleic acid arrays produced thereby, where such reference is made only for ease of description and is in no way intended to limit the scope of the invention as it will be apparent that the subject may be employed with any suitable in situ polymeric synthesis device, e.g., in situ protein synthesis device and the like and may be suitable for the synthesis of a variety of polymeric arrays such as protein arrays and the like. A feature of the subject invention is that an in situ polymeric synthesis device is used to synthesize one or more test probe features on a substrate. The test probe feature(s) are then used to detect any misalignment of the deposition unit, e.g., printheads, of the in situ polymeric array synthesis device, as will be described in greater detail below. As used herein, a printhead may include just one jet or may include a plurality of jets.

Figure 2A:
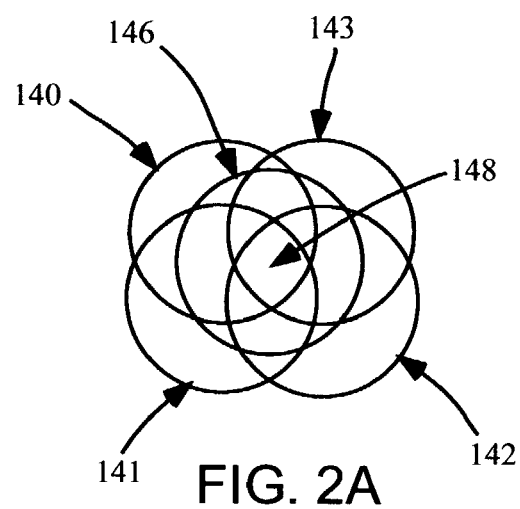
FIG. 2A shows the effects of misalignment of all four printheads of a fluid deposition device relative to each other.
Figure 2B:
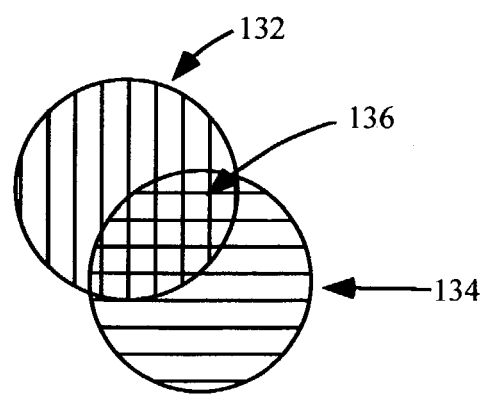
FIG. 2B shows the effects of misalignment between two printheads of a fluid deposition device relative to each other, wherein each printhead delivers two monomers different from the two monomer delivered from the other printhead.

FIG. 2A illustrates the effect of a relative misalignment with respect to the intended position 146, between four independent printheads, each of which deposits one monomer, e.g., herein shown as each depositing one nucleotide. As illustrated, first through fourth drops of reagents 140, 141, 142 and 143 are misaligned. In this example, misalignment occurs at every layer, i.e., each coupling step, such that only the region of commonality between the droplets, herein represented by reference numeral 148, contains the full length intended nucleic acid sequence while four unintended sequences are also produced adjacent thereto. It will be apparent that in practice, all combinations of monomer, e.g., nucleotides, may be produced due to the misalignment, i.e., A, AT, ATC, ATCG, ATG, AC, ACG, AG, T, TC, TCG, TG, C, CG and G. In many instances, two types of monomers, e.g., phosphoramidites, are delivered from a single printhead, as mentioned above. Accordingly, in this case the two phosphoramidites are aligned with respect to each other within the same printhead, but misaligned with respect to the other printhead or rather the other two phosphoramidites delivered from a second printhead. For example, G and T phosphoramidites may be delivered from a first printhead and C and A phosphoramidites may be delivered from a second printhead. Thus, G and T are aligned with respect to each other, but misaligned with respect to C and A. FIG. 2B illustrates the result of such misalignment. As shown, three regions are synthesized: a central region 136 containing the intended full length sequence containing all four intended nucleotides A, C, T and G, and two "crescent" regions (i.e., regions that have shapes analogous to crescent shapes) of unintended sequences containing sequences of G and T only (region 132) and sequences of A and T only (region 134).

In order to automatically scan or read arrays for the presence of radioactively, fluorescently or chemiluminescently labeled targets, it is most desirable for the surfaces of the features to be uniformly covered with desired surface-bound polymers, and for each feature to have a sharply defined edge. The inter-feature areas of the array should have little or no contaminants that can bind the targets, including substrate-bound polymers inadvertently synthesized along with the intended polymers synthesized within the features. Otherwise, after exposure of the array to labeled sample molecules, the inventors have realized that fuzzy, indiscrete area of the array substrate will contain labeled target molecules, making it difficult for the software used to analyze the features to select an area for signal intensity averaging. Poorly averaged signal intensity may significantly lower confidence in resulting measurements, and may even produce incorrect results.

The subject methods may be employed to produce a variety of different test probe features. Generally a test probe feature produced according to the subject invention includes at least two monomers deposited on a substrate surface is a sequential manner to form a polymer or oligomer. In certain embodiments, one or more test probe features is a "di-monomer" meaning that the test probe feature is made up of only two monomers or precursor units used to synthesize the test probe feature and in certain embodiments one or more test probe features is made up of four different monomers. For example, in certain embodiments one or more test probe features is a dinucleotide made up of only two nucleosides, i.e., is an oligo made up of two unique bases, and in certain embodiments one or more test probe features is made up of four different nucleotides. In certain embodiments, a plurality of test probe features are produced on a substrate surface, for example two or more test probe features may be produced at two distinct locations on a substrate, where the test probe features may be the same or may be different.

As noted above, the subject invention will be described herein primarily with reference to producing one or more nucleic acid test probe features on a substrate surface for ease of description only and is in no way intended to limit the scope of the invention. As such, where the test probe features produced are nucleic acid test probe features, such are typically produced according to the subject invention by in situ synthesis using sequential phosphoramidite addition. Phosphoramidite based chemical synthesis of nucleic acids is well known to those of skill in the art, being reviewed above and in U.S. Pat. No. 4,415,732, the disclosure of which is herein incorporated by reference. Generally, in phosphoramidite synthesis of nucleic acids, deoxynucleoside phosphoramidites are used as monomers for the stepwise synthesis of the nucleic acid on a substrate surface. Accordingly, the deoxynucleosides include adenosine, guanosine, cytidine and thymidine, which are added sequentially as fluid droplets from an in situ nucleic acid array synthesis device to a substrate surface such that each sequential monomer is added to the growing oligonucleotide polymer attached to the substrate surface. In further describing the subject invention, a summary of a general phosphoramidite synthesis protocol is generally described to provide a proper foundation for the subject invention. Next, the subject methods will be described, as well as substrates that include one or more subject test probe features and which may also include one or more nucleic acid arrays. Arrays produced according to the subject invention are then described. Finally, kits for use in practicing the subject methods are described.

General Phosphoramidite Synthesis Protocol

Figure 3:
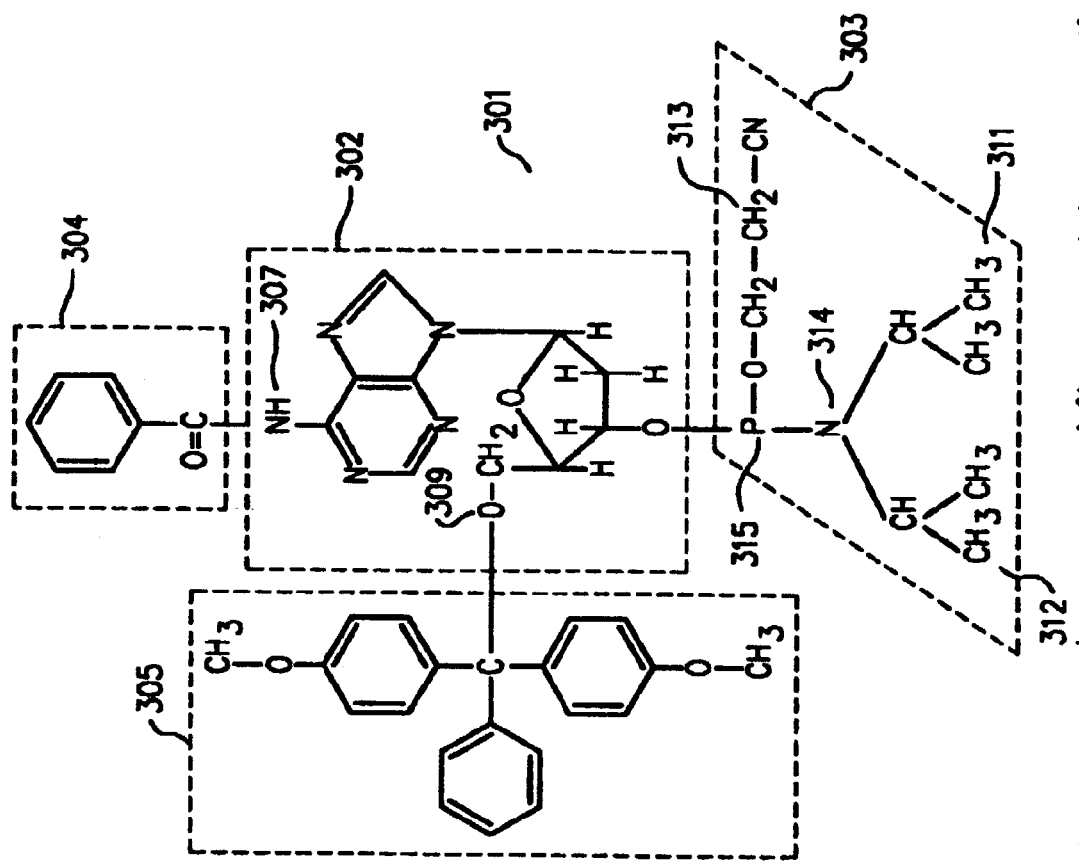
FIG. 3 illustrates the deoxynucleoside phosphoramidite 5'-Dimethoxytrityl-N-benzoyl-2'-deoxyAdenosine, 3'-[(O-cyanoethyl)-(N,N-diisopropyl)]-phosphoramidite.

FIG. 3 illustrates the deoxynucleoside phosphoramidite 5'-Dimethoxytrityl-N-benzoyl-2'-deoxyAdenosine,3'-[(O-cyanoethyl)-(N,N-diisopropyl)]-phosphoramidite. This monomer 301 is composed of four different subcomponent groups 302–305, enclosed in FIG. 2 within dashed lines. The first subcomponent group 302 is a deoxynucleoside. In FIG. 2, the deoxynucleoside illustrated is adenosine. As mentioned above, other deoxynucleoside phosphoramidites used in the synthesis of oligonucleotides contain guanosine, cytidine, and thymidine in place of the adenosine 302 shown in FIG. 3. A benzoyl group 304 is linked through an amide bond to $N^6$ of the adenosine group 302. This benzoyl group protects the primary amine of the adenosine group from reacting with the phosphoramidite group of a second deoxynucleoside phosphoramidite. The primary amines of guanosine and cytidine are similarly protected in the other deoxynucleoside phosphoramidites. Different types of protecting groups are available, including, for example, acetyl or isobutyryl groups. A dimethoxytrityl ("DMTr") group 305 is linked to the 5' end of the deoxynucleoside group in order to protect the 5'-hydroxyl group of the deoxynucleoside from reacting with the phosphoramidite group of another deoxyphosphoramidite. Finally, a phosphoramidite group 303 is linked to the 3' end of the adenosine group 302. A variety of different phosphoramidite groups may be employed in which different types of alkyl groups may be substituted for the isopropyl groups 311–312 linked to the amine nitrogen atom 314 of the phosphoramidite group 303 and the cyanoethyl group 313 linked via a phosphite ester bond to the phosphorous atom 315 of the phosphoramidite group 303.

Figure 4A:
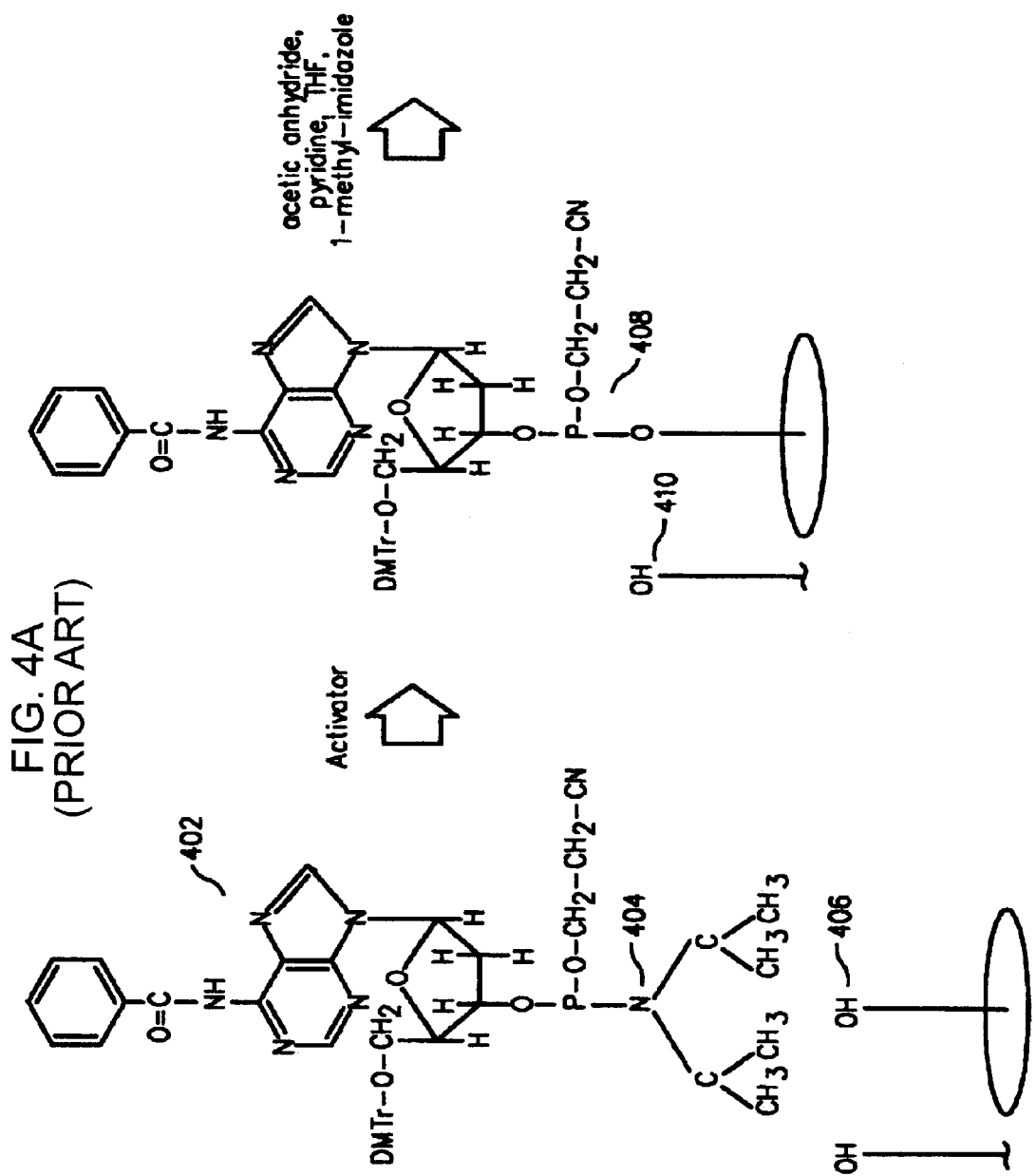
FIGS. 4A and 4B illustrate the chemical steps employed to link a first deoxynucleoside phosphoramidite monomer to a free hydroxyl group on the surface of a substrate.
Figure 4B:
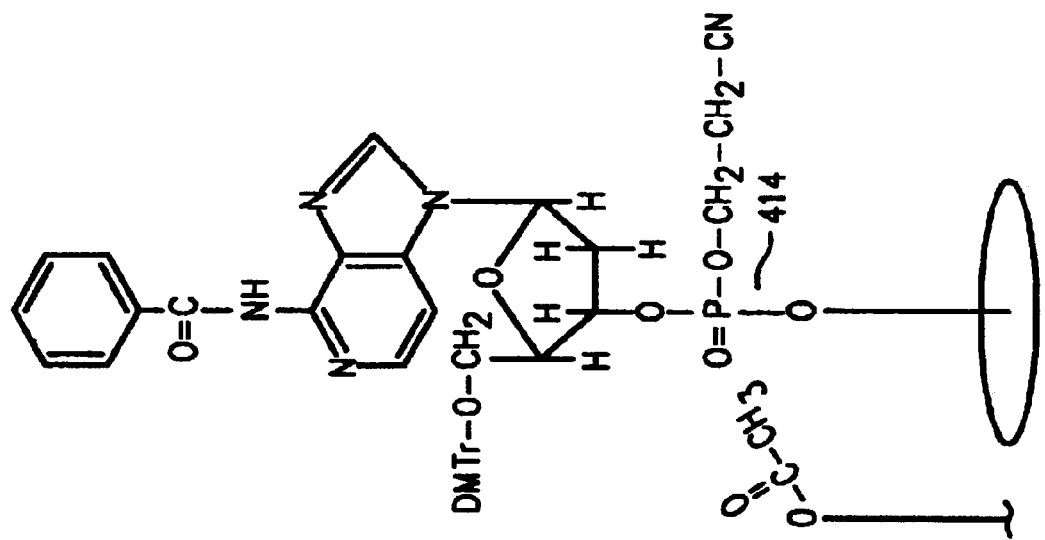
Figure 4B:
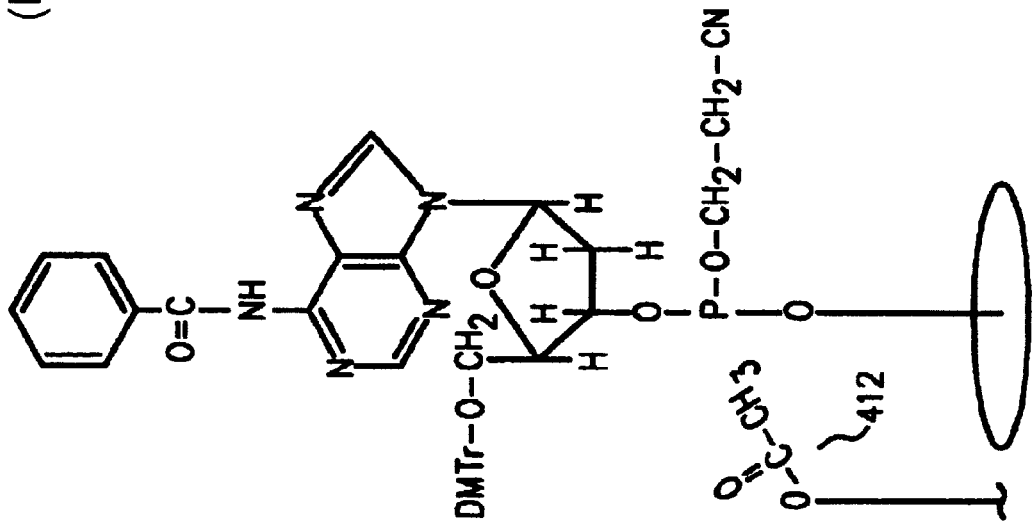

FIGS. 4A and 4B illustrate the chemical steps, as are known in the art, employed to link the first protected deoxynucleoside phosphoramidite monomer to a free hydroxyl group on the surface of the substrate. A solution containing a protected deoxynucleoside phosphoramidite 402 and an activator, such as tetrazole, benzoimidazolium triflate ("BZT"), S-ethyl tetrazole, and dicyanoimidazole, is applied to the surface of the substrate that has been chemically prepared to present reactive functional groups, herein shown as free hydroxyl groups 406. The activators tetrazole, BZT, S-ethyl tetrazole, and dicyanoimidazole are acids that protonate the amine nitrogen 404 of the phosphoramidite group of the deoxynucleoside phosphoramidite 402. A free hydroxyl group 406 on the surface of the substrate displaces the protonated secondary amine group of the phosphoramidite group by nucleophilic substitution and results in the protected deoxynucleoside covalently bound to the substrate via a phosphite triester group 408. Diisopropyl amine is released into solution. After a wash step, in which unreacted deoxynucleoside phosphoramidites, diisopropyl amine, and activator are removed, free hydroxyl groups of the substrate, particularly free hydroxyl groups of the inter-cell regions of the substrate 410, are optionally acetylated 412 by application of a solution of CAP A, comprising acetic anhydride, pyridine or 2,6-lutidine (2,6-dimethylpyridine), and tetrahydrofuran ("THF"), and CAP B, comprising 1-methyl-imidazole in THF. After a wash step, in which the CAP A/CAP B solution is removed, the phosphite triester group is oxidized by the addition of iodine in THF, pyridine, and water to form a phosphotriester group 414.

Figure 5A:
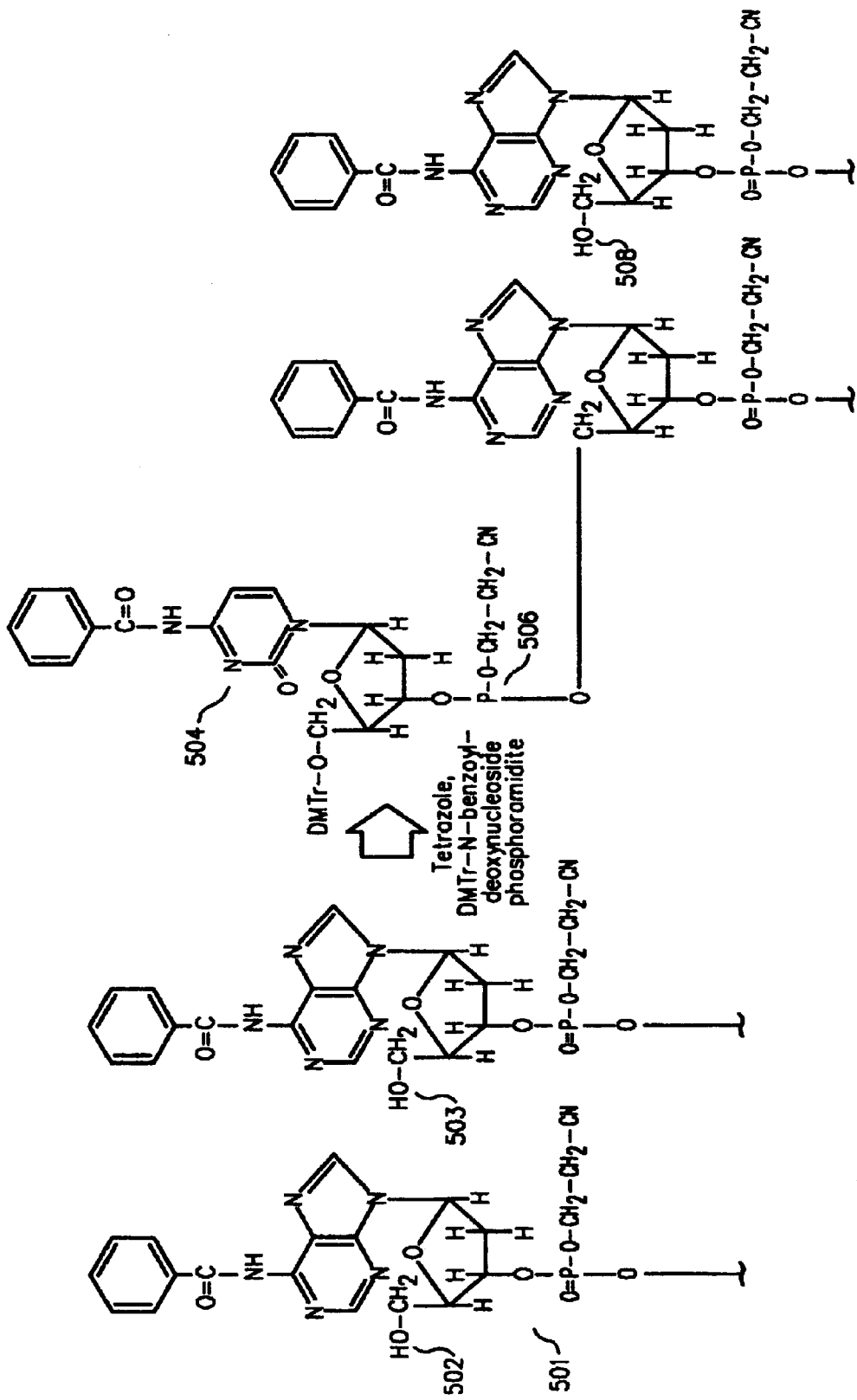
FIGS. 5A and 5B illustrate the addition of a deoxynucleoside phosphoramidite monomer to a growing oligonucleotide polymer bound to the surface of a substrate.
Figure 5B:
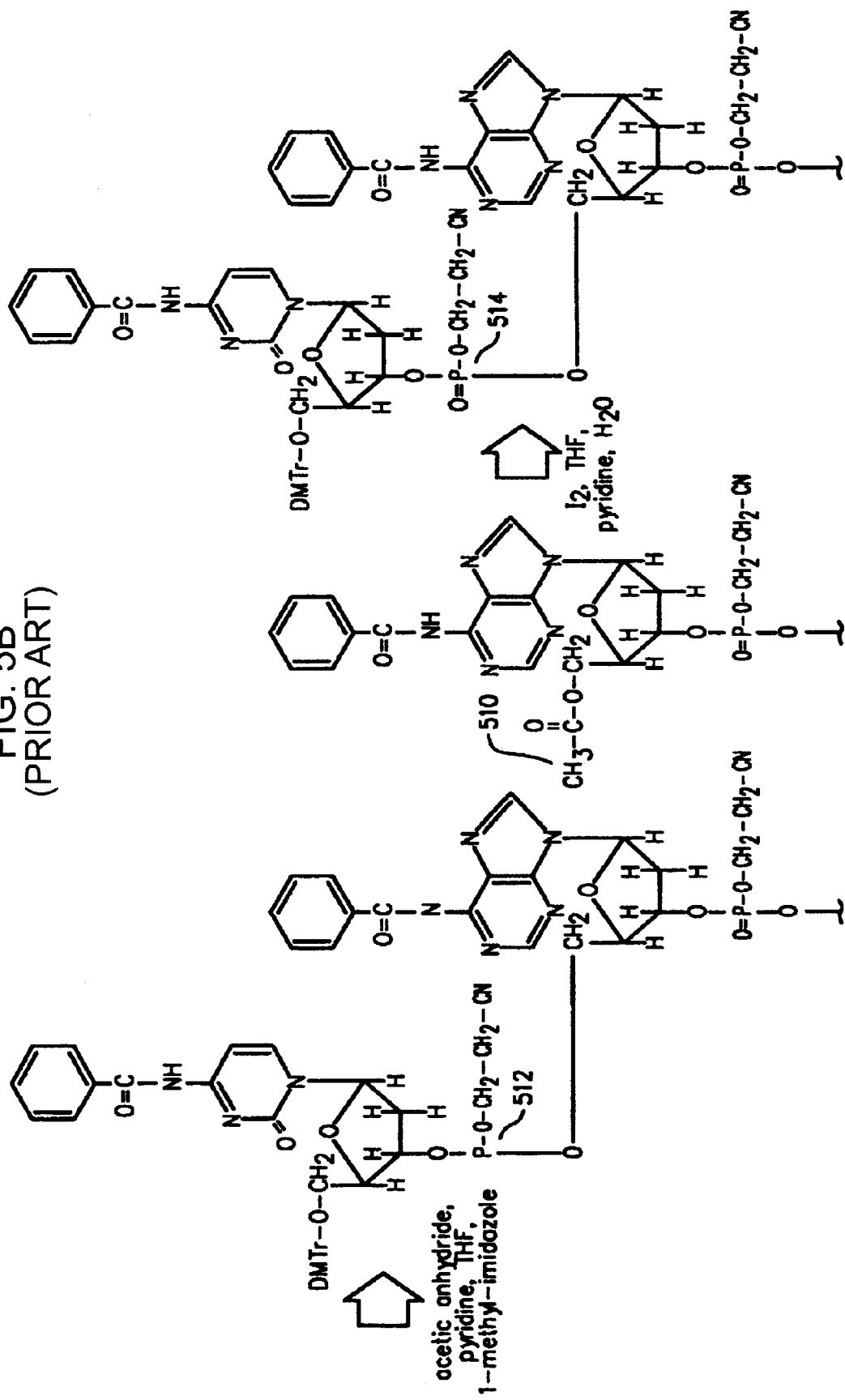

FIGS. 5A and 5B illustrate the addition of a deoxyphosphoramidite monomer to a growing oligonucleotide polymer 501 attached to the surface of the substrate, as is known in the art. After any unreacted reagents from previous synthetic steps are removed by washing, the DMTr protecting groups of the 5'-terminal nucleosides of the growing oligonucleotides are removed by treatment with acid to produce a free 5'-hydroxyl group 502–503. Next, a protected deoxynucleoside phosphoramidite (DMTr-N-benzoyl-deoxyCytidine phosphoramidite in the figure) in solution with tetrazole, or any other known activator, is applied to the substrate-bound oligonucleotide and reacts with the 5' hydroxyl of the oligonucleotide to covalently link the protected deoxynucleoside 504 to the 5' end of the oligonucleotide via a phosphite triester group 506. After excess, unreacted protected deoxynucleoside phosphoramidite and activator are removed by washing, any unreacted 5'-hydroxyl groups 508 of substrate-bound oligonucleotides are acetylated 510 by application of a CAP A (tetrahydrofuran ("THF"), pyridine, and acetic anhydride)/CAP B (methylimidazole in THF) solution. This step may be necessary because the previous oligonucleotide elongation reaction does not proceed to 100% completion, and it may be desirable to terminate any unreacted nucleotides by acetylation so that oligonucleotides with incorrect sequences are not produced in subsequent synthetic steps. After the CAP A/CAP B solution is removed by washing with acetonitrile, the phosphite triester group 512 is oxidized to a phosphotriester group 514 by the addition of $I_2$, THF, pyridine, and $H_2O$. The steps illustrated in FIGS. 5A and 5B are repeated to add each additional deoxynucleoside to the 5' end of the growing oligonucleotide.

Methods of Detecting Printhead Misalignment

In accordance with the subject invention, two or more precursor molecules, i.e., monomers, precursor units or residues such as deoxynucleoside phosphoramidites, are employed to synthesize a test probe at a particular location on a substrate surface using an in situ polymeric synthesis device such as a pulse jet fluid deposition device, e.g., a nucleic acid or protein or polypeptide array synthesis device. Each distinct test probe is typically present as a composition of multiple copies of the test probe on the substrate surface, e.g., as a spot or feature on the surface of the substrate, such that more than one copy of a particular test probe is typically synthesized on a substrate as a test probe spot or test probe feature according to the subject methods. In many embodiments, a plurality of test probe features are synthesized on the same substrate surface, where one or more test probe features may be the same or one or more may be different, e.g., all of the test probe features may be the same or all may be different or some may be different.

A feature of the subject inventions is that these synthesized test probe features are employed to evaluate whether any of the printheads of the in situ nucleic acid array synthesis devices used to synthesize the test probes are misaligned relative to each other. As mentioned above, any printhead misalignment that has occurred during the course of an in situ synthesis protocol using an in situ array synthesis device will produce unintended synthesized sequences in the form of crescent shaped areas as well as the intended sequence where the printheads deposit monomers at a common location. Accordingly, if the deposition unit, e.g., the printheads, of an in situ nucleic acid array synthesis device are misaligned, a test probe synthesized thereby will have unintended sequences in addition to the intended sequence. In accordance with the subject invention, any misalignment, i.e., any sequences that have been unintentionally synthesized due to any printhead misalignment, are easily detected by contacting the one or more test probe features with a sample that includes detectably labeled target nucleic acids that are complementary to the unintended sequences. Thus, any labels that are detected following contact of the test probe feature(s) with such a sample may be directly related to deposition unit, e.g., printhead, misalignment. In other words, the detection of any of these labeled target molecules that have bound to any sequences that have been synthesized due to any printhead misalignment correlates to the printheads that have produced the misalignment.

In accordance with certain embodiments of the subject invention, at least two of the targets employed have distinguishable labels relative to each other. Accordingly, if misalignment occurred during the synthesis of a test probe feature, i.e., if crescent areas or areas of unintended sequences have been synthesized, the distinguishably labeled targets will bind to their complementary unintended sequences, thus distinguishably labeling these unintended sequences by virtue of the complementary targets. Accordingly, upon scanning of the test probe feature, the labels bound thereto provide a manner with which to distinguishably detect any unintentionally synthesized sequences because the targets are distinguishable from each other.

Accordingly, in many embodiments the targets preferentially bind to different polymers, each formed from less than, e.g., less than or equal to about half, of all the precursor units used to synthesize a given test probe feature. The different polymers to which the targets preferentially bind may each be formed from multiple precursor units used to synthesize a given test probe.

Nucleotides and oligomers or polymers formed therewith, e.g., dinucleotides, trinucleotides, etc., of nucleotides, are commonly represented by the upper case letters A, T, C and G, that represent adenosine, thymidine, cytosine and guanosine subunits or monomers, respectively. This convention will be employed in the following discussion.

As described above, an in situ polymeric array synthesis device, e.g., an in situ nucleic acid array synthesis device, typically has either four independent printheads (each having a plurality of nozzles or orifices for monomer deposition therefrom) such that each printhead is configured to deposit a single monomer and each printhead typically, though not necessarily, moves independently of any other printhead or has two pairs of printheads (each printhead having a plurality of nozzles or orifices for monomer deposition therefrom) such that one printhead pair usually deposits two different monomers and the other printhead pair usually deposits two other, different monomers. In the latter case, it is not possible to have any misalignment between the members of a printhead pair, but it is possible to have misalignment between the two printhead pairs. In any event, given all the possible printhead configurations, a number of different printheads may be misaligned relative to each other, i.e., any combination of two printheads may be misaligned with respect to each other.

Accordingly, as will be described in greater detail below, a subject test probe may be a di-monomer, e.g., a dinucleotide of only two nucleotides, i.e., an oligo made of only two unique monomers or bases (e.g., nucleotides), or may be made of four different monomers, e.g., four different nucleotides, i.e., made of four unique monomers or bases (e.g., nucleotides). In those embodiments where the test probes are nucleotides made up of two unique nucleotides, in order to detect any printhead misalignment, such test probes are contacted with two different distinguishable labeled target nucleic acids that are homopolymers. In those embodiment where the test probes are made up of four different nucleotides, in order to detect any printhead misalignment, such test probes are contacted with two different distinguishable labeled target nucleic acids that are made up of two different nucleotides. In this manner, misalignment between any two printheads may be detected.

Figure 1:
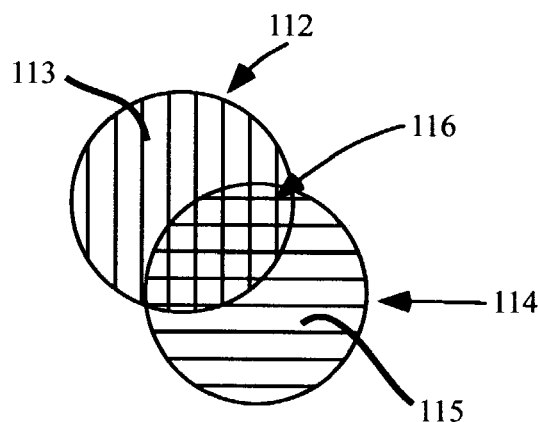
FIG. 1 shows the effects of printhead misalignment of a fluid deposition device during an in situ synthesis using two different monomers.

For example, in certain embodiments intended to detect any printhead misalignment between just two independent printheads, such that a first printhead is used to deliver a first deoxynucleoside phosphoramidite (one of A, C, T or G) and a second printhead is used to deliver a second deoxynucleoside phosphoramidite (one of A, C, T or G). In accordance with the subject invention, a test probe feature is synthesized using these two printheads to detect any misalignment therebetween. If the printheads are misaligned relative to each other, a test probe synthesized thereby will be analogous to that shown in FIG. 1 such that two crescent areas will be produced (of course these areas need not be crescent shapes in all embodiments), each one made up of only one of the nucleosides, along with an area of the intended sequence, i.e., along with an area having both of the first and second nucleosides. Typically, multiple synthesis cycles will be performed such that each of the crescent areas is made up of a homopolymer, i.e., a first crescent is made of one of poly A, poly C, poly T or poly G, depending on the particular nucleoside deposited from the first printhead, and a second crescent is made of one of poly A, poly C, poly T or poly G, depending on the particular nucleoside deposited from the second printhead.

Once the test probe feature is synthesized it is contacted with, in this particular case, a sample containing two different distinguishably labeled target nucleic acids that are homopolymers so that any printhead misalignment may be detected by utilizing the distinguishable labels of any bound targets to the sequences of the crescents. In other words, the sample contacted to the above-described test probe feature includes two different distinguishably labeled target nucleic acids, where each target nucleic acid is complementary to a sequence of one of the crescent areas of the test probe. More specifically, the first labeled target nucleic acid is a homopolymer that is complementary to the unintended sequences of one of the crescent areas and the second labeled target nucleic acid is a homopolymer that is complementary to the other unintended sequences of the other crescent area, where the labels of the targets are distinguishable from each other.

Figure 6A:
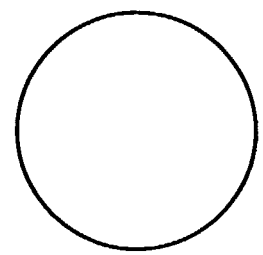
FIGS. 6A and 6B illustrate the steps of an exemplary embodiment of the subject methods employed to detect misalignment between two independent printheads.
Figure 6B:
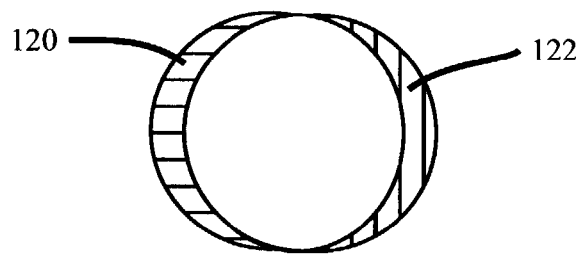

Following the completion of this binding interaction between the test probe feature and the labeled target homopolymers, the test probe feature is scanned to detect any bound labels. FIGS. 6A and 6B illustrate how the above-described methods enable easy detection of any printhead misalignment. FIG. 6A shows the result that would have occurred if there were no misalignment between the two printheads. In this case, because there is no misalignment between the printheads, there were no unintended sequences synthesized, i.e., no crescent areas, and thus there are no test probe sequences that are complementary to either of the target nucleic acid homopolymers so the targets do not bind to the test probe. However, FIG. 6B illustrates the case where the printheads were misaligned. As shown in FIG. 6B, misalignment between the two printheads is detected by detecting the two labels that are bound to the unintended sequences in the two crescent areas. More specifically, a first target nucleic acid having a first label represented by longitudinal lines is bound to the complementary homopolymer of the first crescent area 120 and the second target nucleic acid having a label distinguishable from the first label and represented by horizontal lines is bound to the complementary homopolymer of the second crescent area 122, where the distinguishable labels enable the unintended sequences to be distinguishably detected. Accordingly, scanning the test probe feature after contact with distinguishably labeled target nucleic acids that are complementary to any unintended sequences that may have been synthesized by the particular printhead configuration used, enables any misaligned printheads to be easily detected. In this manner, as will be described in greater detail below, any printhead misalignment that is detected may be corrected prior to using the printheads for other applications, e.g., in situ synthesis of biopolymeric arrays.

The above-described illustration describes an embodiment where the test probe feature made of two precursor units, in this case a dinucleotide made up of only two nucleotides such that the test probe feature is made up of one of: A and C; A and T; A and G; C and T; C and G; or T and G. In this case where the test probe is made up of only two nucleotides, the labeled target molecules complementary to any unintended sequences of these nucleotide test probes are homopolymers, i.e., are poly A, poly C, poly T and poly G, as described above. However, as described above, in certain embodiments, a test probe feature may be made of four different precursor units, e.g., four different nucleotides. In the case where the test probe is made of four different nucleotides, labeled target nucleic acids complementary to any unintended sequences of these test probes are typically made up of two different nucleotides such that these target nucleic acids are made up of at least two of: A and G; A and T; C and G; C and T; A and C; and G and T.

Figure 7A:
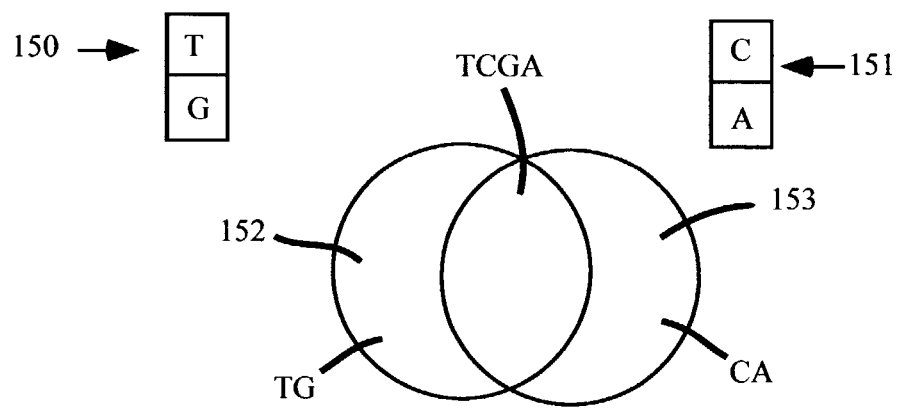
FIGS. 7A and 7B illustrate the steps of an exemplary embodiment of the subject methods employed to detect misalignment between two pairs of printheads.
Figure 7B:
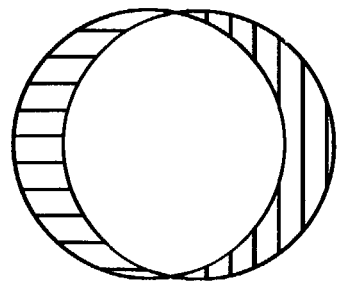

FIGS. 7A and 7B illustrate an exemplary embodiment where a test probe feature made up of four different nucleotides is employed to detect any printhead misalignment. As mentioned above, certain printhead configurations involve two pair of printheads such that a first pair of printheads deposits two different nucleosides and a second pair of printheads deposits two other nucleosides such that all four nucleosides are deposited using the two pair of printheads. In this case, it is not possible to have any misalignment between the nucleosides deposited from the same printhead, but misalignment can occur between the nucleosides of different printheads.

As shown in FIG. 7A, misalignment between the two pairs of printheads 150 and 151 produce unintended sequences made up of T and G in a first crescent area 152 and unintended sequences C and A in the second crescent area 153, as well as the intended sequence made up of all the nucleosides T, C, G, and A in the area of commonality. In a manner analogous to that described above, two distinguishably labeled target nucleic acids complementary to the unintended sequences are contacted with the test probe. As such, each target nucleic acid is made up of two different nucleotides such that a sample that includes at least two of A and G; A and T; C and G; C and T; A and C; and G and T is contacted to the subject test probe feature. In this particular example, a first target nucleic acid is made up of C and A and has a first label (horizontal lines) and a second nucleic acid is made up of G and T (longitudinal lines). FIG. 7B shows the result of the binding of the complementary targets to the unintended sequences, where the distinguishable labels enable the unintended sequences to be detected.

Thus, regardless of the printhead configuration, the first step of the subject methods is to provide a substrate upon which one or more test probe features may be produced, where a variety of solid supports or substrates may be used for such purposes. As will be described below, the substrate upon which one or more test probe features are synthesized may be the same or different from the substrate upon which one or more nucleic acid arrays may be synthesized, for example following evaluation of the misalignment of the printheads of an in situ nucleic acid array synthesis device.

The substrate employed for the test probe feature(s) may be selected from a wide variety of materials including, but not limited to, natural polymeric materials, particularly cellulosic materials and materials derived from cellulose, such as fiber containing papers, e.g., filter paper, chromatographic paper, etc., synthetic or modified naturally occurring polymers, such as nitrocellulose, cellulose acetate, poly (vinyl chloride), polyamides, polyacrylamide, polyacrylate, polymethacrylate, polyesters, polyolefins, polyethylene, polytetrafluoro-ethylene, polypropylene, poly (4-methylbutene), polystyrene, poly(ethylene terephthalate), nylon, poly(vinyl butyrate), cross linked dextran, agarose, etc.; either used by themselves or in conjunction with other materials; fused silica (e.g., glass), bioglass, silicon chips, ceramics, metals, and the like. For example, substrates may include polystyrene, to which short oligophosphodiesters, e.g., oligonucleotides ranging from about 5 to about 50 nucleotides in length, may readily be covalently attached (Letsinger et al. (1975) Nucl. Acids Res. 2:773–786), as well as polyacrylamide (Gait et al. (1982) Nucl. Acids Res. 10:6243–6254), silica (Caruthers et al. (1980) Tetrahedron Letters 21:719–722), and controlled-pore glass (Sproat et al. (1983) Tetrahedron Letters 24:5771–5774). Additionally, the substrate can be hydrophilic or capable of being rendered hydrophilic.

Suitable test probe feature substrates may exist, for example, as sheets, tubing, spheres, containers, pads, slices, films, plates, slides, strips, disks, etc. The substrate is usually flat, but may take on alternative surface configurations. The substrate can be a flat glass substrate, such as a conventional microscope glass slide, a cover slip and the like. Substrates of interest include surface-derivatized glass or silica, or polymer membrane surfaces, as described in Maskos, U. et al., *Nucleic Acids Res,* 1992, 20:1679–84 and Southern, E. M. et al., *Nucleic acids Res,* 1994, 22:1368–73.

Once a suitable substrate is provided, one or more subject test probe features are synthesized thereon using an in situ fluid synthesis device (e.g., an in situ nucleic acid synthesis device) utilizing fluid deposition technology, e.g., using a pulse-jet fluid deposition device as is known in the art, to a location on the surface of the substrate in a sequential or step-wise fashion to produce a test probe feature. In situ synthesis protocols and well as in situ synthesis devices are known in the art (pulse jet as well as other technologies such as pin spotting technologies and acoustical focusing technologies) and are described, for example, in U.S. Pat. Nos. 6,222,030, 6,242,266; 6,300,137; 6,232,072; 6,180,351; 6,171,797; 6,323,043; 6,447,723; 5,028,937; U.S. patent application Ser. No. 09/302,898 filed Apr. 30, 1999 by Caren et al., and the references cited therein, herein incorporated by reference.

Accordingly, the first droplet of a test probe, containing the first deoxynucleoside phosphoramidite that will end up as the 3'-termial nucleoside, defines the position of the location of the intended test probe. One or more subsequent droplets, each having a deoxynucleoside phosphoramidite, are targeted to the same, precise location as the first droplet. However, due to misalignment between the printheads, subsequent droplets may end up being deposited at locations offset from the location of the application of the first droplet. As described above, in accordance with the subject methods, once one or more test probe features are produced on the substrate, the test probe feature(s) are contacted with target nucleic acids having detectable labels such that the target molecules bind to complements of the test probe feature(s) enabling detection of printhead misalignment using the detectable labels that are then bound to the test probe features using the targets.

As mentioned above, in many embodiments more than one test probe feature is synthesized such that misalignment of any printheads may be detected. FIGS. 8A–8E illustrate an exemplary embodiment of the subject methods for producing a plurality of test probes on a substrate surface using four independent printheads that move relative to each other such that misalignment between any two printheads is possible. In accordance with the subject invention, any misalignment of one or more printheads may be detected and, if desired, corrected prior to the in situ synthesis of a nucleic acid array using the printhead(s).

Generally, test probe features of all possible combinations of nucleotides made up of the four nucleotides A, T, C and G may be synthesized using the printheads of the deposition device. Each test probe is then contacted with a sample containing distinguishably labeled target nucleic acids complementary to the possible homopolymers that may be produced due to misalignment for all possible printhead combinations. All the target nucleic acid labels may be distinguishable from one another, i.e., four labels may be distinguishable from each other, such that all possible printhead misalignments may be detected directly or in certain embodiments three distinguishable labels may be employed such that certain printhead misalignments may be indirectly detected based on the detection of the other printhead misalignments. As such, up to six different test probe features may be synthesized representing all two-printhead combinations. For the sake of brevity, the synthesis of a nucleotide test probe made up of A and G is used for exemplary purposes only and is in no way intended to limit the scope of the invention.

FIG. 8A illustrates, in cross section, a substrate 2 positioned on a stage 300, wherein the surface of substrate 2 has been prepared to present reactive functional groups, in this case hydroxyl groups 4, at the surface that will serve as starting points or anchors to which synthesized test probes will be bound. In accordance with the subject invention, the next step is to deposit a fluid droplet containing a monomer onto the substrate surface, as shown in FIG. 8B. The protected adenosine phosphoramidite monomer containing droplet 8, deposited from a first printhead, is shown positioned on the surface of the substrate such that $8_d$ illustrates the diameter of droplet 8 spread out on the substrate surface.

FIG. 8D shows the deposition of a second protected nucleoside phosphoramidite droplet 10 from a second printhead to the substrate surface following a deprotection step (not illustrated), where the diameter of droplet 10 is represented by $10_d$. Although the intended location of second droplet 10 is the precise location of first droplet 8, due to misalignment between the printheads, the second droplet has been applied to a position offset or left of the first droplet, i.e., the second droplet is misaligned with respect to the first droplet. The above described sequential deposition of the two droplets, as well as the sequential deposition of any embodiment of the subject invention, may be repeated one or more times such that the number of times the sequence is repeated is herein represented by "n", where "n" is an integer that ranges from 1 to about 100, usually from about 4 to about 60 and more usually from about 10 to about 40.

A top down view of test probe 28 is shown in FIG. 8E. As a result of misalignment between the two printheads that produced test probe 28, this particular test probe has three distinct regions. The central, core region 18 is the area of the test probe produced where both the printheads deposited monomers at the same location on the substrate such that guanosine phosphoramidite monomers have been added to the 5'-protected adenosine monomers bound to the substrate surface to form $(GA)_n$ nucleotides. Due to misalignment, a second region 16, outside the core region, has been formed that includes surface-bound guanosine monomers or $(G)_n$. Also due to misalignment, a third region 17 has been formed that includes surface-bound adenosine molecules that are unreacted with guanosine molecules and thus this regions is made up of $(A)_n$. Each region may also include some or all of free OH groups.

As described above, in accordance with the subject invention, at least two different distinguishably labeled target nucleic acids are contacted with the test probe under conditions sufficient to promote binding of the labeled target nucleic acids to complementary molecules on the substrate surface. As such, each target nucleic acid is capable of producing a detectable signal. That is, two or more target nucleic acids are labeled, i.e., conjugated or otherwise bound or associated, to or with a detectable molecule, e.g., an optically detectable molecule, such as a fluorescent dye molecule.

Where the label is a fluorescent compound or agent, i.e., the fluorescent label, it is capable of emitting radiation (visible or invisible) upon stimulation by radiation of a wavelength different from that of the emitted radiation, or through other manners of excitation, e.g., chemical or non-radiative energy transfer. Where the detectable label employed includes a fluorescent label, the radiation or light absorbed and emitted from the fluorescent agent, i.e., the response radiation, (the wavelength of the response radiation) is chosen to be in the portion of the electromagnetic spectrum to which the detecting optical apparatus such as an array optical reader or scanner is sensitive. Usually, the light absorbed and emitted from the fluorescent agent is in the ultraviolet, visible or infrared regions, but may include other wavelengths as well as appropriate.

The particular fluorescent agent(s) employed may vary depending on a variety of factors, where such factors include the particular optical scanner used to detect the fluorescence, the excitation and/or response wavelength, and the like. The fluorophoric moieties or fluorophores of the fluorescent agents may be cyclic or polycyclic, particularly polycyclic, aromatic compounds having at least two rings, usually at least three rings and not more than six rings, more usually not more than five-rings, where at least two of the rings are fused and in certain embodiments at least three of the rings are fused, where usually not more than four of the rings are fused. The aromatic compounds may be carbocyclic or heterocyclic, particularly having from one to three, more usually one to two nitrogen atoms as heteroannular atoms. Other heteroannular atoms may include oxygen and sulfur (chalcogen).

The rings may be substituted by a wide variety of substituents, which substituents may include alkyl groups of from one to six carbon atoms, usually from one to two carbon atoms, oxy, which includes hydroxy, alkoxy and carboxy ester, generally of from one to four carbon atoms, amino, including mono- and disubstituted amino, particularly mono- and dialkyl amino, of from 0 to 8, usually 0 to 6 carbon atoms, thio, particularly alkylthio from 1 to 4, usually 1 to 2 carbon atoms, sulfonate, including alkylsulfonate and sulfonic acid, cyano, non-oxo-carbonyl, such as carboxy and derivatives thereof, particularly carboxamide or carboxyalkyl, of from 1 to 8 or 1 to 6 carbon atoms, usually 2 to 6 carbon atoms and more usually 2 to 4 carbon atoms, oxo-carbonyl or acyl, generally from 1 to 4 carbon atoms, halo, particularly of atomic number 9 to 35, etc.

Specific fluorescent agents of interest include, but are not limited to: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G)(emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2-,4-,7-,4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc., BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, etc.

As described above, the target nucleic acids are labeled with labels that are distinguishable from each other upon detection. As such, a first target nucleic acid is labeled with a first detectable label and a second target nucleic acid is labeled with a second label, i.e., a label that is distinguishable from the first detectable label upon detection thereof. In other words, the maximum wavelengths or peaks of the emitted radiation responses from the respective detectable labels will vary. The difference between the wavelengths of the distinguishable labels will depend on the quality of the scanner being employed and the filters used, as well as the particular labels or dyes chosen. Typically, a label is distinguishable from another label if less than about 5%, and usually less than about 1%, of the emitted radiation of the first distinguishable label is detected or recorded as the emitted radiation of the second distinguishable label by the detecting device. In certain embodiments, the maximum wavelengths or peaks of the emitted responses of two distinguishable labels will differ by about 60 nm to about 100 nm or more.

Any combination of suitable detectable agents may be used with the only limitation being that the fluorescent agents are distinguishable from each other upon detection, where particular combinations of interest include fluorescein dyes and cyanine dyes; R6G, i.e., 2-[ethylamino)-3-(ethylimino)-2-7-dimethyl-3H-xanthen-9-yl]benzoic acid ethyl ester monohydrochloride and HIDC, i.e., 1,1,3,3,3',3'-Hexamethylindodicarbocyanine iodide; Cy3 (Indocarbocyanine) and Cy5 (Indodicarbocyanine); TAMRA and Cy5; and other suitable combinations, where combinations of green and red dyes are of particular interest. For example, a first target nucleic acid may be labeled with a fluorescein dye and a second target nucleic acid may be labeled with cyanine dye.

Thus, in accordance with the subject invention, because the target nucleic acid have been labeled with distinguishable labels, unintended sequences complementary to the target nucleic acid that have been synthesized as a result of any printhead misalignment may be easily detected by an appropriate detector device such as an optical detector capable of fluorescent scanning of the solid support. Accordingly, each label will provide a unique fluorescent signal which will enable the spatial location of the labels relative to each other to be easily detected because the labels are distinguishable from one another.

As illustrated in FIG. 8F, test probe 28, for example, is contacted with two different distinguishably labeled target nucleic acids that are complementary to the areas of the test probe that were produced by the printhead misalignment, i.e., area 10 having $(G)_n$ and area 8 having $(A)_n$, such that a first target nucleic acid $(T)_n$ having a first detectable label herein represented as a square with longitudinal lines and a second target nucleic acid $(C)_n$ having a second detectable labeled herein represented by a square with horizontal lines are contacted with the test probe feature under conditions to promote binding of the target to its complement. In the case of hybridization assays, the sample is typically contacted with a test probe under stringent hybridization conditions, such that complexes are formed between the target nucleic acids that are complementary to test probe sequences attached to the array surface, i.e., duplex nucleic acids are formed on the surface of the substrate by the interaction of the test probe nucleic acid and its complement target nucleic acid present in the sample. An example of stringent hybridization conditions is hybridization at about 50° C. or higher and 0.1×SSC (15 mM sodium chloride/1.5 mM sodium citrate). Another example of stringent hybridization conditions is overnight incubation at about 42° C. in a solution: 50% formamide, 5×SSC (150 mM NaCl, 15 mM trisodium citrate), 50 mM sodium phosphate (pH7.6), 5× Denhardt's solution, 10% dextran sulfate, followed by washing the arrays in 0.1×SSC at about 65° C. Hybridization involving nucleic acids generally takes from about 30 minutes to about 24 hours, but may vary as required. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed as appropriate, as well as other less stringent conditions.

Once a test probe feature is exposed to a sample containing the target nucleic acids, incubated and washed, the binding of the test probe feature and the labeled target nucleic acids is then evaluated. Evaluating a test probe feature includes reading the test probe feature. Reading a test probe feature may be accomplished by illuminating the test probe feature and reading the location and intensity of resulting fluorescence of the test probe feature to detect any binding complexes on the surface of the array. For example, a scanner may be used for this purpose which is similar to the AGILENT MICROARRAY SCANNER available from Agilent Technologies, Palo Alto, Calif. Results from the reading may be raw results (such as fluorescence intensity readings for each test probe feature for each color channel) or may be processed results such as obtained by rejecting a reading for a feature which is below a predetermined threshold and/or forming conclusions based on the pattern read from the test probe feature. The results of the reading (processed or not) may be forwarded (such as by communication) to a remote location if desired, and received there for further use (such as further processing, etc.).

As shown in FIG. 8G, regions 16 and 17 will produce two different, distinguishable signals due to the binding of the labeled target thereto. That is, region 16, having a detectable label represented by longitudinal lines will provide a first signal, region 17, having a detectable label represented by horizontal lines will provide a second signal that is distinguishable from the first signal of region 16. Accordingly, the binding of the labeled targets to the test probe may then be evaluated to detect any printhead misalignment of the in situ nucleic acid array synthesis device. As shown in FIG. 8G, the misalignment of the first printhead relative to the second printhead is easily detected by the distinguishable labels bound to the sequences synthesized by the misaligned printheads.

FIG. 8H illustrates all six possible nucleotide test probes that may be synthesized using the four independent printheads in a manner analogous to that described above. As mentioned above, some or all combinations may be synthesized in any embodiments. Accordingly, in this particular example, the test probes are contacted with a sample having four different homopolymer target nucleic acids, where each target nucleic acid has a label that is distinguishable from the other labels. In this manner, printhead misalignment between any two printheads may be directly detected by detecting the distinguishable labels, as shown in FIG. 8H.

However, as described above, some of the target homopolymers may have the same label such that the relative positions of some of the printheads are not able to be directly determined, but may be indirectly determined by the relative comparison to other printheads. As shown in FIG. 9A, in this embodiment all possible combinations of dinucleotides are synthesized as test probes on substrate 2 using the four printheads of an in situ nucleic acid array synthesis device. Accordingly, test probe 71 is synthesized using printheads A and C and includes a region of $(A)_n$, a region of $(C)_n$ and a region of $(AC)_n$. Test probe 72 is synthesized using printheads A and G and includes a region of $(A)_n$, a region of $(G)_n$ and a region of $(AG)_n$. Test probe 73 is synthesized using printheads A and T and includes a region of $(A)_n$, a region of $(T)_n$ and a region of $(AT)_n$. Test probe 74 is synthesized using printheads C and G and includes a region of $(C)_n$, a region of $(G)_n$ and a region of $(CG)_n$, test probe 75 is synthesized using printheads C and T and includes a region of $(C)_n$, a region of $(T)_n$ and a region of $(CT)_n$ and test probe 76 is synthesized using printheads G and T and includes a region of $(G)_n$, a region of $(T)_n$ and a region of $(GT)_n$.

Once the test probes are synthesized, they are contacted with labeled target nucleic acids in a manner analogous to that described above so that they may be evaluated and any printheads that are misaligned may be detected. As mentioned above, printing misalignment may be detected using three labels that are distinguishable from each other. Accordingly, test probes 71, 72, 73, 74, 75 and 76 are contacted with labeled target nucleic acids complementary to sequences that may be produced due to printhead misalignment, i.e., complementary to the possible crescent regions that may be produced at each test probe, such that the complementary target nucleic acids in this example are four different homopolymers.

Specifically, the test probe features may be contacted with a first target nucleic acid of $(C)_n$ having a first label, a second target nucleic acid of $(G)_n$ having the same label as $(C)_n$, a third target nucleic acid of $(A)_n$ having a second label distinguishable from the first and third labels and a fourth target nucleic acid $(T)_n$ having either a third label that is distinguishable from the other two labels or a label that is a mixture of the first two labels so that a two-color label reader may be employed.

The result of the binding of the targets to their complements is shown in FIG. 9B. As shown, evaluating the binding of the targets to their complements provides information about any misalignment between printheads., In this embodiment, the relative positions of printheads C and G with respect to each other cannot be directly determined because the labels are the same. However, the relative positions of printheads C and G with respect to each other can be indirectly determined by relative comparison with the detected signals of the other printheads. In this particular example, all printheads are misaligned relative to each other. However, it will be apparent that in certain instances no printheads, or fewer than all possible printheads, will be misaligned.

As described above, in situ nucleic acid array synthesis devices may employ a variety of printhead configurations for synthesis. For example, in certain embodiments, two pairs of printheads may be employed. FIGS. 10A and 10B illustrate the instance where two pair of printheads are employed and a plurality of different test probes are synthesized.

As noted above, each pair of printheads is used to deposit two types of monomers, e.g., two of A, C, T, or G. In this regard, a first member of a first printhead deposits A nucleosides and a second member of the first printhead deposits C nucleosides and the first member of a second printhead deposits T nucleosides and the second member of the second printhead deposits G nucleosides. As such, the printheads are configured such that no misalignment is possible between the two members of a printhead pair, i.e., in this particular example there is no misalignment possible between the C and A, nor is there any misalignment possible between G and T. Accordingly, the relative position of members C relative to member A and the relative position of member G relative to member T do not need to be determined. However, the relative positions (direction, magnitude and sign) of all other members relative to one another may be easily determined in accordance with the subject methods.

Accordingly, a plurality of test probe features may be synthesized on a substrate using the two printhead pairs of the in situ nucleic acid array synthesis device. In certain embodiments, all possible combinations of nucleotides may be employed (except those where misalignment is not possible) in order to detect all possible misalignments. Accordingly, FIG. 10A shows a top down view of all possible combinations of test probe features synthesized using the two pair of printheads such that all possible nucleotides made of two nucleotides are synthesized as test probes on a substrate 2. As shown, test probe 38 is made up of A and G and includes a region of $(A)_n$, a region of $(G)_n$ and a region of $(AG)_n$. Test probe 48 is made up of A and T and includes a region of $(A)_n$, a region of $(T)_n$ and a region of $(AT)_n$. Test probe 58 is made up of C and G and includes a region of $(C)_n$, a region of $(G)_n$ and a region of $(CG)_n$. Test probe 68 is made up of C and T and includes a region of $(G)_n$, a region of $(T)_n$ and a region of $(CT)_n$.

Once the test probes are synthesized on the substrate, they are contacted with labeled target nucleic acids in a manner analogous to that described above so that they may be evaluated. While each different target nucleic acid may have a different distinguishable label from any other label, printing misalignment in this instance may be detected using fewer than four different labels, each distinguishable from one another, for example two distinguishable labels may be employed. Accordingly, test probes 28, 48, 58 and 68 are contacted with labeled target nucleic acids complementary to sequences that may be produced due to printhead misalignment, i.e., complementary to the crescent regions of each test probe, such that the complementary target nucleic acids in this example are four different homopolymers.

Specifically, a first target nucleic acid of $(T)_n$ having a first label, a second target nucleic acid of $(G)_n$ having the same label as $(T)_n$, a third target nucleic acid of $(A)_n$ having a second label distinguishable from the first label and a fourth target nucleic acid $(C)_n$ having the same label as $(A)_n$, are contacted with the test probes. The result of the binding of the targets to their complements is shown in FIG. 10B. As shown, evaluating the binding of the targets to their complements provides information about any misalignment between printheads. In this particular example, printheads A and G are misaligned relative to each other, printheads A and T are misaligned relative to each other, printheads C and G are misaligned relative to each other and printheads C and T are misaligned relative to each other. However, it will be apparent that in certain instances no printheads, or fewer than all possible printheads, will be misaligned.

FIGS. 11A and 11B illustrate the steps of another exemplary embodiment for detecting any printhead misalignment between two pairs of printheads such that there is no misalignment between the members of each pair, but misalignment may occur between the pairs, as described above. In these embodiments, a single test probe feature may be employed that is made of all four different nucleotides and printhead misalignment may be detected using two target nucleic acids, where each target nucleic acid is made up of two different nucleotides and each target has a label that is distinguishable from the label of the other target.

Accordingly, test probe 80 is synthesized on substrate 2 by depositing G and T nucleosides from a first printhead pair and C and A nucleosides from a second printhead pair. Accordingly, due to misalignment between the two printhead pairs, a first region of $(TG)_n$ is produced, a second region of $(CA)_n$ is produced and a third region of $(TCGA)_n$ is produced corresponding to where the printheads deposit nucleosides at the same location on the substrate.

Once the test probe feature made up of four different nucleotides is synthesized, it is contacted with labeled target nucleic acids in a manner analogous to that described above so that the binding of the target to the probe feature may be evaluated and any printhead misalignment between the pairs of printheads may be detected. Accordingly, test probe 80 may be contacted with just two different, distinguishably labeled target nucleic acids complementary to sequences that may be produced due to printhead pair misalignment. Specifically, the test probe feature may be contacted with a first target nucleic acid of $(AC)_n$ having a first label and a second target nucleic acid of $(GT)_n$ having a second label that is distinguishable from the first label. The result of the binding of these distinguishably labeled targets to their probe complements is shown in FIG. 10B. As shown, evaluating the binding of the targets to their complements provides information about any misalignment between the pairs of printheads. In this example, the pairs of printheads are misaligned.

Regardless of the method employed to detect any printhead misalignment, in accordance with the subject invention one or more printheads may be adjusted if misalignment is detected. Such adjustment include any adjustment of the synthesis protocol that is capable of minimizing misalignment or unintentionally synthesized areas, where such adjustment(s) may be mechanical and/or chemical and/or software-based. For example, an individual printhead may be adjusted and/or a carriage that moves one or more printheads may be adjusted, etc. Such adjustment(s) may be performed manually such as following an operator alert generated by the deposition system or automatically, e.g., by suitable algorithm and hardware and software capable of carrying out the adjustment. In an example of a software correction, the locations of deposited drops may be altered by the software to compensate for the misalignment. Once adjusted, the steps of the subject methods may be repeated to verify that the one or more adjusted printhead is aligned. In many embodiments, the subject methods and subsequent printhead alignment correction is performed in a manufacturing setting. For example, the subject methods may be easily incorporated into nucleic acid array manufacturing protocols such that prior to using a particular in situ nucleic acid array synthesis device in the manufacture of one or more nucleic acid arrays, the subject methods may be employed to detect any printhead misalignment. If any misalignment is detected, the printheads may be adjusted before any nucleic acid array synthesis is performed using the printheads of the in situ nucleic acid array synthesis device, or the misalignment noted for future reference.

However, the subject invention is not limited to the manufacturing setting, but may also be employed at a user or customer site. In such instances, a substrate having one or more test probe features may be provided to a user of one or more nucleic acid arrays. The test probe features may be test probes synthesized prior, during or after the manufacture of the one or more nucleic acid array using the same in situ nucleic acid array synthesis device that was used to synthesize the one or more nucleic acid arrays. In certain embodiments, the one or more test probe features may be synthesized on the same substrate as the one or more arrays or on a different substrate. Accordingly, employing the subject methods to detect any printhead misalignment using the test probe feature(s) may provide useful information about the array assay performed with the one or more nucleic acid array to the user. In certain embodiments, such information may be correlated to a correction factor or the like used in the analysis of the array assay results of the one or more nucleic acid arrays.

Arrays Produced According to the Subject Methods

Also provided by the subject invention are arrays of polymers, e.g., nucleic acids, polypeptides, etc, produced according to the subject methods such that arrays may be produced using an in situ nucleic acid array synthesis device that has been or will be evaluated according to the subject methods for any printhead misalignment. The arrays may be synthesized using the in situ nucleic acid array synthesis device following printhead adjustment, if misalignment is detected according to the subject methods and/or an array assay correction factor may be provided that addresses any printhead misalignment, e.g., a mathematical correction that may be used in analyzing array assay results, array assay reagent adjustments, etc. That is, a plurality of polymers (oftentimes referred to as probes, binding agents or members of a binding pair in this context) covalently bonded to a substrate surface in the form of an "array" or pattern is provided. Such arrays find use in a variety of applications, including gene expression analysis, drug screening, nucleic acid sequencing, mutation analysis, and the like.

The subject arrays include at least two distinct polymers that differ by monomeric sequence attached to different and known locations on the substrate surface. Each distinct polymeric sequence of the array is typically present as a composition of multiple copies of the polymer on a substrate surface, e.g., as a spot or feature on the surface of the substrate. The number of distinct polymeric sequences, and hence spots or similar structures, present on the array may vary, where a typical array may contain more than about ten, more than about one hundred, more than about one thousand, more than about ten thousand or even more than about one hundred thousand features in an area of less than about 20 $cm^2$ or even less than about 10 $cm^2$. For example, features may have widths (that is, diameter, for a round spot) in the range from about 10 μm to about 1.0 cm. In other embodiments, each feature may have a width in the range from about 1.0 μm to about 1.0 mm, usually from about 5.0 μm to about 500 μm and more usually from about 10 μm to about 200 μm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10% or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents, but may not be present when, for example, photolithographic array fabrication process are used. It will be appreciated though, that the interfeature areas, when present, could be of various sizes and configurations. The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

In the broadest sense, the arrays are arrays of polymeric or biopolymeric ligands or molecules, i.e., binding agents. In many embodiments of interest, the arrays are arrays of nucleic acids, including oligonucleotides, polynucleotides, cDNAs, mRNAs, synthetic mimetics thereof, and the like.

Each array may cover an area of less than about 100 $cm^2$, or even less than about 50 $cm^2$, 10 $cm^2$ or 1 $cm^2$. In many embodiments, the substrate carrying the one or more arrays will be shaped generally as a rectangular solid (although other shapes are possible), having a length of more than about 4 mm and less than about 1 m, usually more than about 4 mm and less than about 600 mm, more usually less than about 400 mm; a width of more than about 4 mm and less than about 1 m, usually less than about 500 mm and more usually less than about 400 mm; and a thickness of more than about 0.01 mm and less than about 5.0 mm, usually more than about 0.1 mm and less than about 2 mm and more usually more than about 0.6 mm and less than about 1.5 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least about 20%, or about 50% (or even at least about 70%, 90%, or 95%), of the illuminating light incident on the substrate as may be measured across the entire integrated spectrum of such illuminating light or alternatively at 532 nm or 633 nm. As noted above, the substrates that carry the subject arrays may also carry one or more test probe features.

Utility

The subject arrays find use in a variety of different applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with a subject array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, Internet, etc.

As such, a subject array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER available from Agilent Technologies, Palo Alto, Calif. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

Kits

Finally, kits for detecting printhead misalignment of an in situ nucleic acid array synthesis device are provided. The subject kits at least include one or more test probe features on a substrate. The subject kits may include two or more labeled target nucleic acids, e.g., distinguishably labeled target nucleic acids, as described above. In certain embodiments, the subject kits may also include one or more components for preparing nucleic acid targets and/or for labeling nucleic acids with a detectable label, e.g., sample preparation reagents, labels, buffers and the like. The kit may further include one or more containers such as vials or bottles, with each container containing a separate component for carrying out a printhead misalignment detection assay. The kit may also include a denaturation reagent for denaturing the target, buffers, wash mediums, enzyme substrates, negative and positive controls and written instructions for using the subject test probe features for carrying out the evaluation of a test probe feature, i.e., for carrying out a binding assay between a test probe feature and target nucleic acids for detecting any printhead misalignment. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

The kit may further include one or more nucleic acid arrays which may be present on the same substrate as a test probe or on another substrate. Accordingly, the kits may further include one or more additional components necessary for carrying out an array assay, e.g., an analyte detection assay, for use with the arrays, such as sample preparation reagents, buffers, labels, and the like. As such, the kits may include one or more containers such as-vials or bottles, with each container containing a separate component for the array assay, and reagents for carrying out an array assay such as a nucleic acid hybridization assay or the like. The kit may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the subject array assay devices for carrying out an array based assay. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

Experimental

The following example is put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

The quantification of the printhead misalignment of a pulse-jet fluid deposition device (Agilent Technologies, Inc., Palo Alto, Calif.) containing two printheads and two phosphoramidite reservoirs per printhead was performed as follows. In this particular example, G and T phosphoramidites were used as coupling reagents in a first printhead, while C and A phosphoramidites were used as coupling reagents in a second printhead. A microarray containing 25,760 features in a 1027 mm$^2$ area was synthesized on a planar substrate based on standard phosphoramidite chemistry using the fluid deposition device. In this protocol, the phosphoramidite coupling was controlled spatially by deposition of the appropriate phosphoramidite reagent using the printheads. The oxidation, deblock and, optionally, capping reactions, were performed in flowcells in a non spatially controlled manner. The oligonucleotide sequence 3'-CCTATGTGACTGGTC-GATGCTACTA (SEQ ID NO:01) was synthesized in individual features on the same microarray using three different alignments between the two printheads. Alignment no. 1 was synthesized without any adjustment of the printheads. In Alignments nos. 2 and 3, the printheads were adjusted to compensate for misalignment. Each feature was repeated up to 8000 times. The sequences of the remaining features were quality control probes routinely synthesized on arrays.

After synthesis and standard post-treatment (deprotection of the base protecting groups, washes, etc.), the microarray was hybridized for 2 hours at 25° C. using Agilent Technologies hybridization kit (Agilent product number 5184-3568) and a mixture of 10 pM 5'-Cy5-AACACACCACA-CAA (SEQ ID NO:02) and 5'-Cy3-GGTTGGTGTGT (SEQ ID NO:03) as labeled sample. This labeled target was complementary to the sequences of the crescent areas or the areas unintentionally synthesized due to misalignment. After washing and drying, the microarray was scanned using an Agilent microarray scanner. As shown in FIG. 12A, the fluorescent signals were detected to have crescent shapes (white arrows show Cy3 signal and grey arrows show Cy5 signal) indicating the location of the probe sequences 3'-TTGTGTGGTGTGTT (SEQ ID NO:04) and 3'-CCAAC-CACACA (SEQ ID NO:05) resulting from the misplacement of the phosphoramidite reagents due to the original misalignment of the two printheads. The sizes of the crescent areas demonstrate that the alignment obtained using alignment no. 2 was superior to the alignment obtained with alignment no. 1, but inferior to the alignment obtained with alignment no. 3.

FIG. 12 also demonstrates how this method may be used to empirically optimize printhead alignment. As a control, another array was synthesized and processed with the identical process parameters, with the exception that the hybridization target, which was a 1:1 mixture of 5'-GGATACACT-GACCAGCTACGATGAT (SEQ ID NO:06) (full length complementary target) labeled at the 5' end with Cy3:Cy5, was intended to be complementary to the intentionally synthesized sequence or rather the center areas. FIG. 12B shows that, as expected, the effective size of the area containing the full-length probe sequence, reported by the fluorescent signal, is increasing as the amplitude of misalignment decreases.

EXAMPLE 2

Analogous to example 1, the quantification of the printhead misalignments of a pulse-jet fluid deposition device (Agilent Technologies, Inc.) containing four printheads and one phosphoramidite reservoir per printhead was performed with the following modifications. Because the relative misalignment of each printhead with respect to all other printheads must be determined, the following sequences were synthesized using the same reaction parameters as in example 1: 5' or 3'-(AC)$_{12}$(SEQ ID NO:07), 5' or 3'-(AG)$_{12}$(SEQ ID NO:08), 5' or 3'-(AT)$_{12}$(SEQ ID NO:09), 5' or 3'-(CG)$_{12}$(SEQ ID NO:10), 5' or 3'-(CT)$_{12}$(SEQ ID NO:11), and 5' or 3'-(GT)$_{12}$(SEQ ID NO:12), as well as 5' or 3'-(AA)$_{12}$(SEQ ID NO:13), 5' or 3'-(CC)$_{12}$(SEQ ID NO:14), 5' or 3'-(GG)$_{12}$(SEQ ID NO:15) and 5' or 3'-(TT)$_{12}$(SEQ ID NO:16) as controls. The target sequences utilized during hybridization were modified to contain 3'-(G)$_{12}$-Cy5 (SEQ ID NO:17), 3'-(C)$_{12}$-Cy5 (SEQ ID NO:18), 3'-(T)$_{12}$-Cy5 (SEQ ID NO:19), 3'-(A)$_{12}$-Cy3 (SEQ ID NO:20), and 3'-(T)$_{12}$-Cy3 (SEQ ID NO:21). Accordingly, the fluorescent signals obtained for each feature were unambiguously determined and indicated the relative misalignment between the two printheads used for the synthesis of the particular sequence. An exception is the feature with the sequence 5' or 3'-(CG)$_{12}$ (SEQ ID NO:10), which was used to determine the amplitude, but not the direction of the misalignment between the two printheads. However, this direction was indirectly determined by comparison of the other printhead misalignments found using other sequences (for instance by comparing 5' or 3'-(AC)$_{12}$(SEQ ID NO:07) and 5' or 3'-(AG)$_{12}$)(SEQ ID NO:08).

It is evident from the above results and discussion that the above described invention provides an important new protocol for detecting printhead misalignment of an in situ nucleic acid array synthesis device. The above described invention provides for a number of advantages including ease of use, cost effectiveness and effectiveness at detecting printhead misalignments. The subject invention also enables immediate detection and/or adjustments of one or more printheads of an in situ nucleic acid array synthesis fluid deposition device if misalignment is detected. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method of detecting deposition unit misalignment of an in situ polymeric array synthesis device, said method comprising:
synthesizing at least one test probe feature on a substrate using said in situ polymeric array synthesis device;
contacting said at least one test probe feature with at least two different distinguishably labeled targets; and
evaluating the binding of said two different distinguishably labeled targets to said at least one test probe feature to detect any pulse jet misalignment of said in situ polymeric array synthesis device.

2. The method according to claim 1, wherein said targets preferentially bind to different polymers each formed from less than all precursor units used to synthesize the at least one test probe feature.

3. The method according to claim 2, wherein the different polymers to which the targets preferentially bind are each formed from multiple precursor units used to synthesize the at least one test probe feature.

4. The method according to claim 3, wherein the different polymers to which the targets preferentially bind are each formed from no more than half the precursor units used to synthesize the at least one test probe feature.

5. The method according to claim 2, wherein different sub-sets of the precursor units used to synthesize the at least one test probe feature are deposited from different printheads, and wherein the different polymers to which the targets preferentially bind are formed from the different sub-sets of the precursor units so that printhead misalignment is detected by the evaluating.

6. The method according to claim 5, wherein said deposition units are pulse jets.

7. A method of detecting printhead misalignment of an in situ nucleic acid array synthesis device, said method comprising:
   synthesizing at least one test probe feature on a substrate using said in situ nucleic acid array synthesis device;
   contacting said at least one test probe feature with at least two different distinguishably labeled target nucleic acids; and
   evaluating the binding of said two different distinguishably labeled target nucleic acids to said at least one test probe feature to detect any printhead misalignment of said in situ nucleic acid array synthesis device.

8. The method according to claim 7, wherein said at least one test probe feature is made up of only two nucleotides chosen from the group of A, C, T and G.

9. The method according to claim 8, wherein said synthesizing comprises synthesizing two or more test probe features chosen from the group of A and C; A and G; A and T; C and G; C and T; T and C; and G and T.

10. The method according to claim 7, wherein said at least two different distinguishably labeled target nucleic acids are homopolymers.

11. The method according to claim 10, wherein said at least two different distinguishably labeled target nucleic acids comprise four different homopolymers.

12. The method according to claim 11, wherein said four different homopolymers comprise poly A, poly C, poly T and poly G.

13. The method according to claim 10, wherein at least two of said homopolymers are labeled with the same label.

14. The method according to claim 13, wherein three of said homopolymers are labeled with the same label.

15. The method according to claim 7, wherein said at least one test probe feature comprises four different nucleotides.

16. The method according to claim 15, wherein said at least two different distinguishably labeled target nucleic acids are made up of two different nucleotides chosen from the group of A and G; A and T; C and G; C and T; A and C; and G and T.

17. The method according to claim 7, further comprising adjusting one or more printheads if misalignment is detected.

18. The method according to claim 7, further comprising synthesizing at least one nucleic acid array on a substrate using said in situ nucleic acid array synthesis device.

19. The method according to claim 18, wherein said at least one nucleic acid array synthesis occurs after adjusting one or more printheads based on said evaluating.

20. The method according to claim 18, wherein said at least one nucleic acid array is synthesized on the same substrate as said at least one test probe feature.

21. The method according to claim 7, wherein said distinguishable labels are fluorescent.

22. The method according to claim 7, wherein said evaluating comprises optically scanning said substrate surface.

23. A method of synthesizing at least one nucleic acid array using an in situ nucleic acid array synthesis device, said method comprising:
   detecting any printhead misalignment of said in situ nucleic acid array synthesis device according to claim 7,
   adjusting any detected printhead misalignment of said in situ nucleic acid array synthesis device; and
   synthesizing at least one nucleic acid array using said in situ nucleic acid array synthesis device.

24. A method of detecting the presence of an analyte in a sample, said method comprising:
   (a) contacting a sample suspected of comprising said analyte with a nucleic acid array synthesized according to claim 23;
   (b) detecting any binding complexes on the surface of the said array to determine the presence of said analyte in said sample using said binding complex data.

25. The method according to claim 24, wherein said method further comprises a data transmission step in which a result from a reading of the array is transmitted from a first location to a second location.

26. The method according to claim 25, wherein said second location is a remote location.

27. A method comprising receiving data representing a result of a reading obtained by the method of claim 25.

* * * * *

SEQUENCE LISTING

```
<160> NUMBER OF SEQ ID NOS: 21

<210> SEQ ID NO 1
<211> LENGTH: 25
<212> TYPE: DNA
<213> ORGANISM: Homo sapien

<400> SEQUENCE: 1
cctatgtgac tggtcgatgc tacta                                        25

<210> SEQ ID NO 2
<211> LENGTH: 14
<212> TYPE: DNA
<213> ORGANISM: Homo sapien

<400> SEQUENCE: 2
aacacaccac acaa                                                    14

<210> SEQ ID NO 3
<211> LENGTH: 11
<212> TYPE: DNA
<213> ORGANISM: Homo sapien

<400> SEQUENCE: 3
ggttggtgtg t                                                       11

<210> SEQ ID NO 4
<211> LENGTH: 14
<212> TYPE: DNA
<213> ORGANISM: Homo sapien

<400> SEQUENCE: 4
ttgtgtggtg tgtt                                                    14

<210> SEQ ID NO 5
<211> LENGTH: 11
<212> TYPE: DNA
<213> ORGANISM: Homo sapien

<400> SEQUENCE: 5
ccaaccacac a                                                       11

<210> SEQ ID NO 6
<211> LENGTH: 25
<212> TYPE: DNA
<213> ORGANISM: Homo sapien

<400> SEQUENCE: 6
ggatacactg accagctacg atgat                                        25

<210> SEQ ID NO 7
<211> LENGTH: 24
<212> TYPE: DNA
<213> ORGANISM: Homo sapien
```

```
<400> SEQUENCE: 7
acacacacac acacacacac acac                                          24

<210> SEQ ID NO 8
<211> LENGTH: 24
<212> TYPE: DNA
<213> ORGANISM: Homo sapien

<400> SEQUENCE: 8
agagagagag agagagagag agag                                          24

<210> SEQ ID NO 9
<211> LENGTH: 24
<212> TYPE: DNA
<213> ORGANISM: Homo sapien

<400> SEQUENCE: 9
atatatatat atatatatat atat                                          24

<210> SEQ ID NO 10
<211> LENGTH: 24
<212> TYPE: DNA
<213> ORGANISM: Homo sapien

<400> SEQUENCE: 10
cgcgcgcgcg cgcgcgcgcg cgcg                                          24

<210> SEQ ID NO 11
<211> LENGTH: 24
<212> TYPE: DNA
<213> ORGANISM: Homo sapien

<400> SEQUENCE: 11
ctctctctct ctctctctct ctct                                          24

<210> SEQ ID NO 12
<211> LENGTH: 24
<212> TYPE: DNA
<213> ORGANISM: Homo sapien

<400> SEQUENCE: 12
gtgtgtgtgt gtgtgtgtgt gtgt                                          24

<210> SEQ ID NO 13
<211> LENGTH: 24
<212> TYPE: DNA
<213> ORGANISM: Homo sapien

<400> SEQUENCE: 13
aaaaaaaaaa aaaaaaaaaa aaaa                                          24

<210> SEQ ID NO 14
<211> LENGTH: 24
<212> TYPE: DNA
<213> ORGANISM: Homo sapien

<400> SEQUENCE: 14
cccccccccc cccccccccc cccc                                          24

<210> SEQ ID NO 15
<211> LENGTH: 24
<212> TYPE: DNA
<213> ORGANISM: Homo sapien
```

```
<400> SEQUENCE: 15
gggggggggg gggggggggg gggg                                      24

<210> SEQ ID NO 16
<211> LENGTH: 24
<212> TYPE: DNA
<213> ORGANISM: Homo sapien

<400> SEQUENCE: 16
tttttttttt tttttttttt tttt                                      24

<210> SEQ ID NO 17
<211> LENGTH: 12
<212> TYPE: DNA
<213> ORGANISM: Homo sapien

<400> SEQUENCE: 17
gggggggggg gg                                                   12

<210> SEQ ID NO 18
<211> LENGTH: 12
<212> TYPE: DNA
<213> ORGANISM: Homo sapien

<400> SEQUENCE: 18
cccccccccc cc                                                   12

<210> SEQ ID NO 19
<211> LENGTH: 12
<212> TYPE: DNA
<213> ORGANISM: Homo sapien

<400> SEQUENCE: 19
tttttttttt tt                                                   12

<210> SEQ ID NO 20
<211> LENGTH: 12
<212> TYPE: DNA
<213> ORGANISM: Homo sapien

<400> SEQUENCE: 20
aaaaaaaaaa aa                                                   12

<210> SEQ ID NO 21
<211> LENGTH: 12
<212> TYPE: DNA
<213> ORGANISM: Homo sapien

<400> SEQUENCE: 21
tttttttttt tt                                                   12
```